Figure 1:
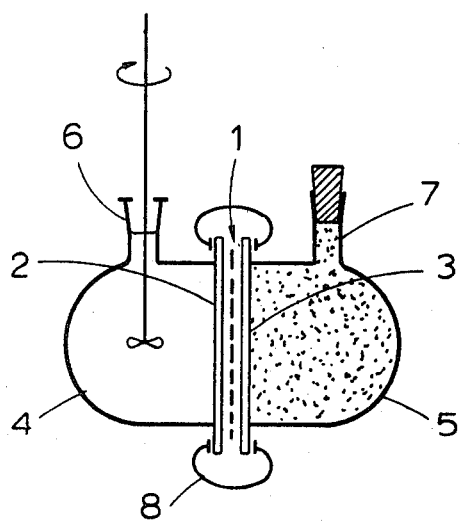

United States Patent [19]

Byrne

[11] 4,092,117

[45] May 30, 1978

[54] DEVICE AND METHOD FOR MONITORING THE METAL CONTENT OF AQUEOUS SYSTEMS

[75] Inventor: Geoffrey Arthur Byrne, Gifford, Scotland

[73] Assignee: Inveresk Research International, Musselburgh, England

[21] Appl. No.: 712,251

[22] Filed: Aug. 6, 1976

[30] Foreign Application Priority Data

Aug. 13, 1975 United Kingdom ............... 33693/75

[51] Int. Cl.² ...................... G01N 31/22; G01N 33/18
[52] U.S. Cl. ................................ 23/230 R; 23/253 R; 210/22 R
[58] Field of Search ......................... 23/230 R, 253 R; 210/22, 96 M; 55/16

[56] References Cited

U.S. PATENT DOCUMENTS

| | | | |
|---|---|---|---|
| 2,411,238 | 11/1946 | Zender | 210/22 |
| 3,182,043 | 5/1965 | Kirkland | 210/22 X |
| 3,495,943 | 2/1970 | Kapff | 210/96 M X |
| 3,749,646 | 7/1973 | Pirt | 210/22 X |
| 3,809,537 | 5/1974 | Horine | 23/230 R |
| 3,935,096 | 1/1976 | Eng et al. | 210/22 C |

*Primary Examiner*—Robert M. Reese
*Attorney, Agent, or Firm*—William R. Liberman

[57] ABSTRACT

A device and method are provided for monitoring the metal content of aqueous systems. The device involves the use of a porous membrane permeable to the metal ions to be detected in an aqueous phase and an organic liquid medium containing a trapping agent for the ions and capable of forming therewith a complex soluble in the organic liquid medium. The organic medium with its trapping agent is contained in a housing with an opening covered by the membrane which can be presented to the aqueous phase.

The device and method allow the aqueous and organic phases to wet opposite faces of the membrane so that ion transfer can take place across the membrane. The trapped ions are analyzed at intervals by conventional means.

7 Claims, 24 Drawing Figures

Pore in hydrophilic membrane.

Pore in hydrophobic membrane.

First Design

Second Design

DEVICE AND METHOD FOR MONITORING THE METAL CONTENT OF AQUEOUS SYSTEMS

The present invention relates to a device and method for monitoring the metal content of water systems. In particular, the device and method can be used to monitor the concentrations or variations in concentration of metals toxic to aquatic life which are derived from effluent discharged into rivers, estuaries and seas, or derived from other sources.

There is worldwide concern over environmental pollution by toxic metals which may be discharged to rivers, estuaries and seas. Although these metals may be present in small quantities, it is known that they do accumulate in aquatic plants and fish. Particular concern has been expressed about toxic metals such as lead and mercury, and complexing ions such as copper, zinc and cadmium which are capable of precipitating protein during the oval stage of fish development.

It is desirable to know whether there is an accumulation of such metals over an extended period of time and to what extent any accumulation can be related to effluent composition, tidal behaviour and river flow. It is also desirable to establish a relationship between the accumulated total of metal collected at any point over a known period of time and the average concentration in water passing that point during that period. An aid to the identification and quantification of metals present in very low concentrations in aqueous streams (information not easily obtained by conventional analysis of 'grab' samples) is also highly desirable.

Accordingly the present invention provides a device and method for monitoring the metal content of a water system, the device comprising a housing provided with an opening, a porous membrane adapted to act as a permeable aqueous medium - organic medium interface, means for securing said membrane to said housing at said opening to constitute a permeable ion barrier at said opening, an organic liquid medium within said housing filling said housing to a level at which said organic liquid medium wets said membrane and a trapping agent within said organic liquid medium capable of forming with at least one class of metal ions diffusing across from an aqueous medium in contact with the outside of said membrane, a complex soluble in said organic liquid medium.

For optimum operation it is preferred that the device should not be adversely effected by changes in, for example, pH, temperature, solids content and biological and chemical oxygen demand of the water.

The device is constructed to withstand variations in underwater currents and able to operate under a range of hydrostatic pressures. In general, the membrane has to be sufficiently robust to withstand knocks from fast moving solid objects in the water. Also, the membrane should not biodegrade during its working life.

The device is designed so that the metal ions from the water under test can diffuse through the membrane at sufficiently high rates to allow accumulation of significant quantities of metal ions within a relatively short time. However, the 'trapping' agent should not become saturated with reacted metal ions during the working life of the device which acts as a metal ion accumulator.

The trapping agent and organic liquid medium, preferably a solvent therefor are so chosen that the concentrations of the trapping agent and trapped metals are not significantly reduced by back-diffusion through the membrane. Similarly, significant losses of the organic liquid medium from the device should not occur.

The trapping agent is chosen to react quickly, quantitatively and irreversibly with the metal ions.

The device should be capable of specifically accumulating one metal or selectively accumulating several metals. It should not be swamped by metals of no interest which may be present in considerably larger quantities than those metals which are of interest. The trapped metals should be readily processed for analysis once removed from the environment under test.

A preferred system comprises an accumulator or monitoring device having a glass housing provided with an opening fitted with a regenerated cellulose membrane (Cupraphane; ex J. P. Bemberg; dry thickness — 10 $\mu$m; pore size — 0.003 $\mu$m; water wet thickness — 20 $\mu$m) and filled with a solution of dithizone in carbon tetrachloride (10 - 400 mg/l). Dithizone is a compound of the formula:

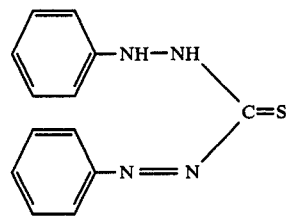

[see "Solvent Extraction of Metals", De, Khopkar and Chalmers, Van Nostrand Reinhold Co. (1970)].

Dithizone reacts with a range of metals including the toxic heavy metals: copper, zinc, or mercury, cadmium and lead, which we are particularly interested to monitor. Carbon tetrachloride is the preferred organic liquid medium or solvent because it is an efficient medium for metal — dithizone reactions, it has a very low solubility in water (significant losses of carbon tetrachloride from the accumulator do not occur in practice) and it is effective in preventing biodegradation of the cellulose membrane (this effect occurs at the water — membrane — solvent interface; in the absence of carbon tetrachloride, the cellulose membrane is biodegraded in river water).

The laboratory work and the field trials together with the conclusions reached are now discussed.

We refer first to the laboratory tests, and in particular to the experimental conditions.

1. Apparatus

Figure 2:
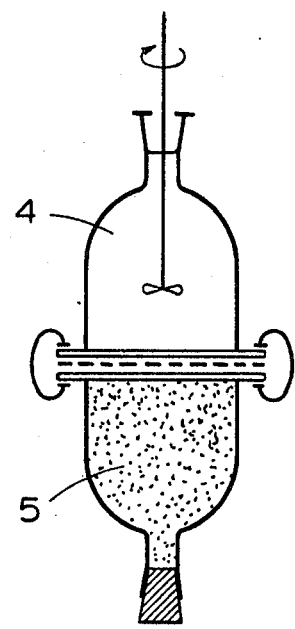

The apparatus used is shown in FIGS. 1 and 2 of the accompanying drawings.

FIG. 1 is a highly diagrammatic elevation of a glass container with a vertical membrane.

A polymer membrane 1 in sheet form is located between the ground glass flanges 2 and 3 of two glass reaction vessels 4 and 5, respectively. Each flask is fitted with a side arm 6 and 7 for filling, stirring (when required) and sampling purposes. To prevent leakage at the flange joints, the membrane is located between two thin polythene gaskets (not shown) heat sealed at their outer perimeter, and the two flasks are held together by spring clips 8. Although chlorinated hydrocarbons have a slight softening effect on polyethylene at room temperature, no adverse effects were noted; if necessary PTFE gaskets, which are completely unaffected by chlorinated hydrocarbons, could be used instead. Vessel 4 contained an aqueous mercuric chloride solution and vessel 5 a solution of dithizone in carbon tetrachloride.

To prevent unwanted transfer of trapping agent or aqueous metal ion solution through the membrane during the filling operation, it was necessary to fill both compartments simultaneously while maintaining approximately equal pressures on either side of the membrane. This was done by keeping the organic layer about 4 cm lower than the aqueous layer until the "aqueous compartment" was full and stoppered.

This system was entirely satisfactory for experiments with cellophane membranes. However, PTFE membranes with large pores (10 μm diameter) sometimes allowed small amounts of chloroform to pass into the aqueous compartment. To obviate this effect, the accumulator shown in FIG. 2 of the accompanying drawings was designed. This design is similar to that of FIG. 1. Due to the greater density of the organic phase, the transfer of organic solvent into the aqueous compartment did not occur unless the aqueous compartment was stirred so vigorously that the resulting vortex "sucked" organic liquid through the membrane.

TABLE A.

| MEMBRANE | Dry Thickness μm | Wet Thickness, μm H₂O | Wet Thickness, μm CCT₄ | Approx. Pore Size μm | Approx. Pore Area % of total membrane area |
|---|---|---|---|---|---|
| Cupraphane (J.P. Bemberg) | 10 | 20 | — | 0.003 | 80 |
| PVC based polymer (Millipore URWP, Solvinert) | 135 | 135 | 135 | 1.5 | 80 |
| PTFE(Millipore LSWP) | 80 | 80 | 80 | 5 | 80 |
| PTFE(Millipore LCWP) | 70 | 70 | 80 | 10 | 80 |

Additional information on trapping agents and membranes is set out below, solely by way of example.

| Trapping Agent - solvent | Metal extracted (examples only) |
|---|---|
| Cupferron (ammonium salt of N-nitrosophenyl hydroxylamine) in chloroform, benzene, ether | bismuth cobalt copper (II) mercury (II) lead zinc zirconium |
| Acetylacetone (solvents as above plus carbon tetrachloride) | aluminium beryllium copper (II) |
| Dibenzoylmethane (solvents as above) | iron (II) thorium zirconium cobalt (III) copper (II) zinc |
| Thenoyltrifluoroacetone (benzene) | aluminium cerium copper (II) lead |
| 8-Hydroxyquinoline (chloroform and solvents as above) | silver cadmium mercury (I), (II) lead zinc |
| Benzildioxime (chloroform) | cobalt (II) copper (II) nickel |
| 1-(2-pyridylazo)-2-naphthol (chloroform, isoamyl alcohol) | cobalt (III) copper (II) iron (III) mercury (II) |

In principle, any polymeric membrane material which is chemically unaffected by the organic solvent (and by water) may be used. The usefulness of membranes which are swollen by the organic solvent will depend upon the degree of swelling and whether prolonged swelling results in slow dissolution or mechanical breakdown of the membrane.

Thus, for example, the so-called Gelman (trade mark) filters in Tables B and C below may be used for those solvents with the code G (e.g. triacetate membrane may be used with an accumulator containing carbon tetrachloride but not with one containing chloroform).

Although hydrophobic membranes such as polypropylene can be made to work, we prefer hydrophilic membranes.

TABLE B.

| | CHEMICAL COMPATIBILITY OF GELMAN FILTERS | | | | | | | |
|---|---|---|---|---|---|---|---|---|
| | Filter | | | | | | | |
| Chemical | Triacetate Metricel Type GA, Type P.E.M. Coloured Metricel | Vinyl Metricel | Fluoride Metricel, Type VF | Alpha Metrical | Acropor, Type AN | Acropor, Type WR | Epoxy Versapor | Polypropylene |
| ALCOHOL | | | | | | | | |
| Methanol | F | G | G | G | G | G | G | G |
| Ethanol | G | G | G | G | G | G | G | G |
| Isopropanol | G | G | G | G | G | G | G | G |
| Propanol | G | G | G | G | G | G | G | G |
| Butanol | G | G | G | G | G | G | G | G |
| Amyl | G | G | G | G | G | G | G | G |
| Tetrahydrofurfuryl | | | | | P | G | | |
| ESTERS | | | | | | | | |
| Methyl Acetate | D | P | F | G | P | F | G | G |
| Ethyl Acetate | P | P | F | G | F | F | G | G |
| Isopropyl Acetate | P | P | G | G | G | G | G | G |
| Butyl Acetate | P | P | G | G | G | G | G | G |
| Amyl Acetate | F | G | G | G | G | G | G | G |
| Cellosolve Acetate | P | P | G | G | G | G | G | G |
| KETONES | | | | | | | | |
| Acetone | P | P | P | G | P | P | G | G |
| Methyl Ethyl Ketone | D | P | F | G | P | F | G | G |
| Methyl Isobutyl Keytone | P | P | G | G | F | G | G | G |
| Cyclohexanene | D | D | P | G | P | P | G | G |
| GLYCOLS | | | | | | | | |

TABLE B.-continued
CHEMICAL COMPATIBILITY OF GELMAN FILTERS

| Chemical | Triacetate Metricel Type GA, Type P.E.M. Coloured Metricel | Vinyl Metricel | Fluoride Metricel, Type VF | Alpha Metrical | Acropor, Type AN | Acropor, Type WR | Epoxy Versapor | Polypropylene |
|---|---|---|---|---|---|---|---|---|
| Ethylene | G | G | G | G | G | G | G | G |
| Propylene | G | G | G | G | G | G | G | G |
| Glycerine | G | G | G | G | G | G | G | G |
| GLYCOL ETHERS | | | | | | | | |
| Methyl Cellosolve | P | F | G | G | G | G | G | G |
| Butyl Cellosolve | F | F | G | G | G | G | G | G |
| ETHERS (MISC.) | | | | | | | | |
| Diethyl | G | G | G | G | G | G | G | G |
| Petroleum | G | G | G | G | G | G | G | G |
| Diisopropyl Ether | | | | | G | | | G |
| Tetrahydrofuran | D | D | P | G | P | P | G | G |
| Dioxane | D | P | P | G | P | P | G | G |
| HALOGENATED HYDROCARBONS | | | | | | | | |
| Chloroform | D | P | G | G | F | G | G | G |
| Methylene Chloride | D | D | G | G | P | G | G | G |
| Carbon Tetrachloride | G | G | G | G | G | G | G | G |
| Trichlorethylene | G | F | G | G | G | G | G | G |
| Freon **TF | G | G | G | G | G | G | G | G |
| Perchloroethylene | G | G | G | G | G | G | G | G |
| Chlorothene ***NU | G | F | G | G | G | G | G | G |
| Gensolv *D | | | | | G | | | G |
| Dowclene ***WR | G | F | G | G | G | G | G | G |
| AROMATIC HYDROCARBONS | | | | | | | | |
| Benzene | G | P | G | G | G | G | G | G |
| Toluene | G | P | G | G | G | G | G | G |
| Xylene | G | P | G | G | G | G | G | G |
| Naphthalene | G | P | G | G | G | G | G | G |

CODE
G = Good, no effect.
F = Fair, swells, softens, slow solvent action.
P = Poor, not recommended. Destroys filter perosity.
D = Dissolves completely.
** = Trade Mark, E.I. DuPont.
*** = Trade Mark, Dow Chemical Co.
* = Trade Mark, Applied Chemical Co.

TABLE C
PROPERTIES OF GELMAN MEMBRANES AND FILTERS

| | Mean Flow Pore Size (Microns) | Polymer |
|---|---|---|
| Triacetate Metricel | | |
| GA-1 | 5 | |
| GA-3 | 1.2 | |
| GA-4 | 0.8 | |
| GA-6 | 0.45 | Cellulose |
| GA-8 | 0.2 | Triacetate |
| GA-9 | 0.1 | |
| GA-10 | 0.05 | |
| P.E.M. | 0.0075 | |
| Coloured Metricel | | |
| Green-4 | 0.8 | |
| Green-6 | 0.45 | Cellulose |
| Black-4 | 0.8 | Triacetate |
| Black-6 | 0.45 | |
| Alpha Metricel | | |
| Alpha-6 | 0.45 | Regenerated |
| Alpha-8 | 0.2 | Cellulose |
| Fluoride Metricel VF-6 | 0.45 | Fluoro-Vinyl |
| Vinyl Metricel | | |
| VM-1 | 5 | Vinyl |
| VM-4 | 0.8 | Vinyl |
| VM-6 | 0.45 | Vinyl |
| Acropor | | |
| AN-3000 | 3 | Acrylonitrile |
| AN-1200 | 1.2 | Polyvinylchloride |
| AN-800 | 0.8 | Copolymer |
| AN-450 | 0.45 | |
| WR | 0.5 | Fluorinated Vinyl |
| (All Acropor grades listed, reinforced with nylon fabric) | | |
| Epoxy Versapor | | |
| 6424 | 5 | Epoxy Glass |
| 6429 | 0.9 | Epoxy Glass |
| Glass Fibre | | |
| Type E | 99.95 DOP* | Glass/Acrylic |
| Type A | 99.95 DOP* | Glass |
| Polypropylene | 10 | Polypropylene |
| Activated Charcoal | | |
| AC-1 | N/A | Cellulose |
| Acid-Washed Paper W-41 | N/A | Cellulose |

*=Pore size designation is inappropriate tested to retain 99.95% DOP at face velocity of 5 cm sec.

NOTE
[1]The Gelman membranes are made by the Gelman Instrument Co. Ann Arbour, Michigan, U.S.A.
[2]Triacetate = cellulose triacetate vinyl metricel type VM is a polyvinyl chloride. Fluoride metricel, type VF is polyvinylidene fluoride. Alpha metricel is a regenerated (from rayon) cellulose acropor type and is an acrylonitrile-polyvinylchloride copolymer reinforced with nylon.

3. Assembly

The cupraphane membranes contained about 17% glycerol as plasticiser. Before assembly, the glycerol was removed by soaking the membrane in distilled water for 30 minutes and then replacing the water by two successive portions of distilled water. The wet membrane was then stretched tightly on an embroidery hoop and, still in the wet condition, fitted onto the accumulator. Both compartments of the accumulator were then filled. Any small amount of water remaining on the surface of the 'trapping side' of the membrane became detached during filling and floated to the top of the organic liquid from where it was easily removed with a pipette.

In stirred systems, the stirrer (of the double link glass variety) was located centrally in the relevant compartment. Although this system does not provide exactly reproducible turbulence from experiment to experiment, it is believed that the conditions achieved were such that valid conclusions could be drawn from the results.

Temperature control is effected by locating the accumulator in a constant temperature ($\pm$ 0.5° C) water bath. In some cases, accurate temperature control was not maintained, and 24 hour experiments were conducted in a laboratory whose temperature varied over 5° C (high during the day, low at night). It was felt that this temperature variation would not markedly affect the conclusions drawn from the results.

4. Measurement of Membrane Thickness

Dry and wet membrane thicknesses were measured with a micrometer.

5. Analysis

The accumulation of $Hg^{2+}$ by the trapping agent was not measured directly. Instead, it was estimated from the measured depletion of $Hg^{2+}$ from the aqueous compartment. Samples were taken from the aqueous compartment of the accumulator at regular intervals using a pipette fitted with a suction device. In order to maintain constant volume conditions, an equal volume of aqueous mercuric chloride of known concentration was then added to the accumulator.

In order to minimise the adsorption of $Hg^{2+}$ onto glass, the pH of the sample was reduced to about 1 by the addition of hydrochloric acid. Samples were then analysed for mercury by the well-known method of cold vapour (flameless) atomic absorption spectroscopy.

Briefly, ionic mercury is reduced to elemental mercury with stannous chloride according to the reaction:

$$Hg^{2+} + Sn^{2+} \rightarrow Hg^{\circ} + Sn^{4+}$$

The liberated mercury is evaporated in a cold stream of air and estimated from its absorption at 253.7nm.

6. Decontamination

Glassware (including accumulators) was decontaminated by washing successively in 50% hydrochloric acid, 20% stannous chloride solution and distilled water.

7. Synthesis of polymeric water swellable membranes

Water swellable membranes were made by both chemical and irradiation cross-linking techniques.

We now refer to the theoretical background.

(a) Surface properties of polymer membranes

Figure 3:
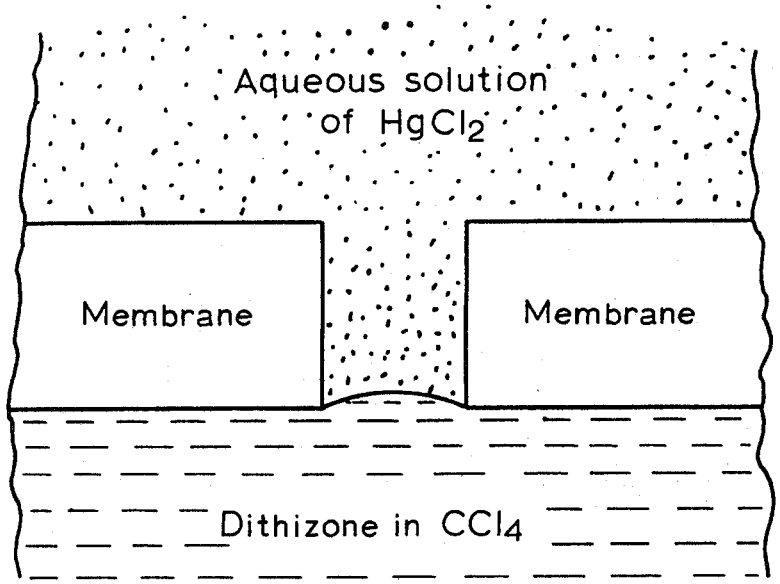
Figure 3:
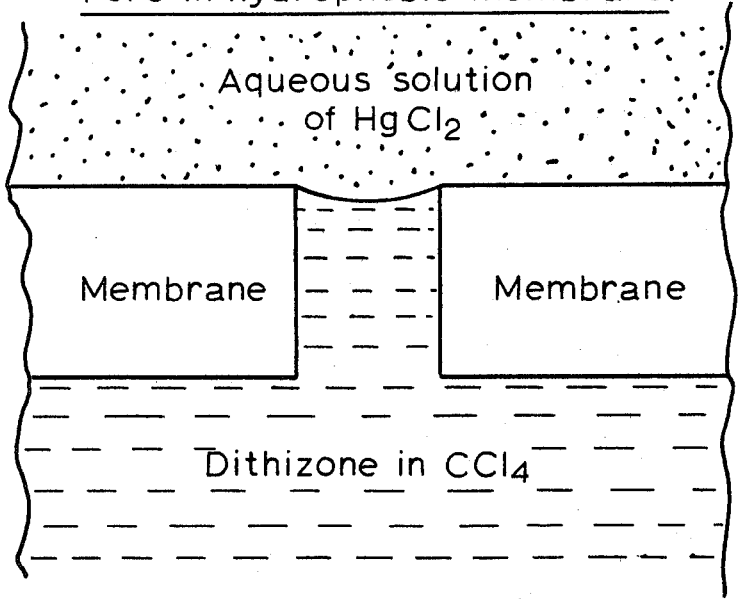

In the case of two different membranes, one made from cellophane (regenerated cellulose) and the other from polytetrafluorothylene -(PTFE), the polymers have different surface properties (surface energies). Cellophane is hydrophilic and therefore more easily wetted by water than by carbon tetrachloride. PTFE is hydrophobic and more easily wetted by carbon tetrachloride than by water. These properties are likely to determine the location of the aqueous-organic liquid interface in the proposed accumulator systems which, in turn, may affect the rate of transfer of metal ions across the membrane. The two systems may be represented as shown in FIG. 3 of the accompanying drawings. Thus, for a hydrophobic membrane the aqueous-organic liquid interface is nearer to the aqueous compartment of the accumulator; the opposite is true for the hydrophilic membrane. Stirring of the fluid in the aqueous compartment increases the rate of transfer of $Hg^{2+}$ ions across both hydrophilic and hydrophobic membranes. However, the effect of stirring on the rate of transfer will be greater if the aqueous-organic liquid interface is nearer to the stirred compartment (i.e., with a hydrophobic membrane) for the following reasons. Consider the transfer of $Hg^{2+}$ ions through membrane pores as shown in FIG. 3. With the hydrophobic membrane, the relevant sequence of events is:

(1) the formation of mercury dithizonate at the aqueous-organic liquid interface; and (2) diffusion of mercury dithizonate through the organic liquid in the pore and thence into the bulk of the organic liquid.

With the hydrophilic membrane the relevant sequence of events is:

(1') the diffusion of $Hg^{2+}$ ions through the stationary water in the pore; and (2') the formation of mercury dithizonate at the aqueous-organic liquid interface and diffusion into the bulk of the organic liquid.

The rate of stirring is unlikely to affect diffusion through stationary liquid in the pores and if it is assumed that the kinetics of events (2) and (1') are similar, then it can be seen that transfer through a hydrophobic membrane should be faster than through a hydrophilic one. However, other properties may determine the choice of membrane, e.g., organic solvent may be lost more easily through a hydrophobic membrane due to the greater proximity of the water-organic interface to the exterior of the device.

(b) Diffusion Kinetics

The well-known diffusion equation:

$$- dm/dt = D.A. \, dc/dx \qquad (i)$$

in which:

$dm/dt$ = rate of transfer of metal ions across the porous barrier into the accumulator D = diffusion coefficient of metal ion in aqueous solution (a value of $10^{-6} cm^2 sec^{-1}$ is suggested as a realistic value for the $Hg^{2+}$ ion).

A = area of the polymer barrier in contact with the fluid at the polymer-aqueous solution interface.

$dc/dx$ = concentration gradient of the metal ion across the barrier (assuming that the metal ion reacts immediately with the trapping agent, dc = concentration of metal ion in feed, and $dc/dx$ for a 1 cm thickness of polymeric barrier is equivalent to the metal ion concentration approaching the barrier), is applied to diffusion of metal ions across a polymer membrane between an aqueous solution and an organic solvent containing a trapping agent.

It is assumed that the diffusion of the metal ions is essentially independent of hydrostatic pressure, and that pressure differences resulting in solvent flow will not exist across the polymer membrane barrier.

Thus, for $Hg^{2+}$ ions in natural uncontaminated sea water, whose typical concentration is $3 \times 10^{-5}$ mg $l^{-1}$ ($3 \times 10^{-11}$ g.cm$^{-3}$)

$$\frac{dm}{dt} = \frac{10^{-6} \times 1 \times 3 \times 10^{-11}}{1} \text{g sec.}^{-1}$$
$$= 7.9 \times 10^{-5} \mu g \text{ month}^{-1}$$

This is the estimated rate of transfer (= rate of accumulation) of $Hg^{2+}$ ions through a 1 cm thick polymer barrier and is somewhat low for practical consideration. However, the rate of transfer of any metal ion across a polymeric barrier of the type under consideration is inversely proportional to the thickness of the barrier. Thus, for a 0.002 cm (20 μm) thick polymer barrier (i.e. similar in thickness to some of the experimental polymer barriers to be described), the rate of transfer of $Hg^{2+}$ ions across a 1 cm² area would be $$\frac{dm}{dt} = \frac{10^{-6} \times 1 \times 3 \times 10^{-11}}{0.002}$$
$$= 1.5 \times 10^{-14} \text{ g. sec}^{-1}$$
$$= 1.29 \times 10^{-9} \text{ g. day}^{-1} \text{ (for 1 cm}^2 \text{ barrier)}$$
$$= 3.87 \times 10^{-8} \frac{g}{month}$$

This rate would be proportionally higher if the cross-sectional area of the polymer barrier were greater. For example, for a 44 cm² cross-sectional area (as in various experimental barriers studied)

$$dm/dt = 1.29 \times 10^{-9} \times 44 \text{ g.day}^{-1}$$
$$= 5.676 \times 10^{-8} \text{ g.day}^{-1}$$
$$= 1.7 \times 10^{-6} \text{ g.month}^{-1} = 1.7 \times 10^{-3} \text{ mg/month}$$

therefore for 1000 sq.cm.: $3.87 \times 10^{-5}$ g/month = $3.87 \times 10^{-2}$ mg/month.

These calculations are based on the very low concentration of $Hg^{2+}$ in natural uncontaminated sea water. In contaminated water, the rate of accumulation of $Hg^{2+}$ (or any other metal ion) is proportionately higher and well within the range of the sensitive analytical procedures we have adopted.

These calculations demonstrated the technical feasibility of the concept.

The above diffusion equation (i) applies to the diffusion of $Hg^{2+}$ ions in solution (D = diffusion coefficient of $Hg^{2+}$ in aqueous solution.) In considering the diffusion of $Hg^{2+}$ ions across the polymer membrane, the equation is modified to:

$$-dm/dt = p^1 A \, dc/dx \quad \text{(ii)}$$

where $P^1$ = specific permeability coefficient of the membrane with units of cm² sec⁻¹

$dc/dx$ = concentration gradient of $Hg^{2+}$ across the membrane. In fact:

$$P^1 = k D_m \quad \text{(iii)}$$

where $k$ = the distribution coefficient of $Hg^{2+}$ between membrane and feed solution and $D_m$ = diffusion coefficient of $Hg^{2+}$ in the membrane (i.e. in the bound water of the membrane). For a membrane of finite thickness $dc/dx \to \Delta C/\Delta X$ ($\Delta X$ is the wet membrane thickness). Since it is assumed that $Hg^{2+}$ ions react immediately with dithizone at the aqueous-organic interface.

$$C = C_{feed} - C_{trapped}$$
$$= C_{feed} = C \text{ in general case}$$

This is a good approximation at the initial stage of any accumulator experiment, provided there is sufficient dithizone present to complex $Hg^{2+}$ at a rapid rate.

$$-dm/dt = P.A.C. \quad \text{(iv)}$$

where $P = P^1/\Delta x$ = membrane permeability with units of cm.sec⁻¹.

Now $dm = dc \times V_o$. Substituting into equation (iv), we get:

$$-dc/C = P.A./V_o \cdot dt \quad \text{(v)}$$

If equation (v) is integrated between the limits $C = C_o$ (time = O) and $C = C_t$ (time = $t$), we get:

$$\int_{C_o}^{C_t} \frac{dc}{C} = - \int_o^t \frac{P.A.}{V_o} dt \quad \text{(vi)}$$

$$\therefore \log C_t = - \frac{P.A.}{2.303 \, V_o} t + \log C_o \quad \text{(vii)}$$

Thus, a plot of log $C_t$ against $t$ should be a straight line of negative slope = $P.A./2.303 \, V_o$ and intercept = log $C_o$.

This result would also indicate that the diffusion followed first order kinetics. Equation (vii) has been used to analyse experiments in which the depletion of $Hg^{2+}$ from the aqueous compartment (rather than the accumulation of $Hg^{2+}$ by the trapping agent) has been followed.

(c) Effect of temperature

The effect of temperature on mass transport of $Hg^{2+}$ ions across the membrane by diffusion can be estimated approximately from the following equation $$D = Ae^{-E/RT} \quad \text{(viii)}$$

where

D = diffusion coefficient of the $Hg^{2+}$ in aqueous solution

A = a constant

T = absolute temperature

R = universal gas constant

E = activation energy for the diffusion of the $Hg^{2+}$ ion in aqueous solution (a figure of 5 Kcal. mole⁻¹ is suggested as realistic). The difference in mass transport between 20° and 25° C is therefore estimated as follows:

$$D_{298} = Ae^{-E/298R}$$
$$D_{293} = Ae^{-E/293R}$$

Therefore $$D_{298}/D_{293} = 1.154$$

Therefore $$P_{209}/P_{293} = 1.154$$

since membrane permeability is directly proportional to diffusion coefficient.

(d) Boundary Layer Effects

Figure 4:
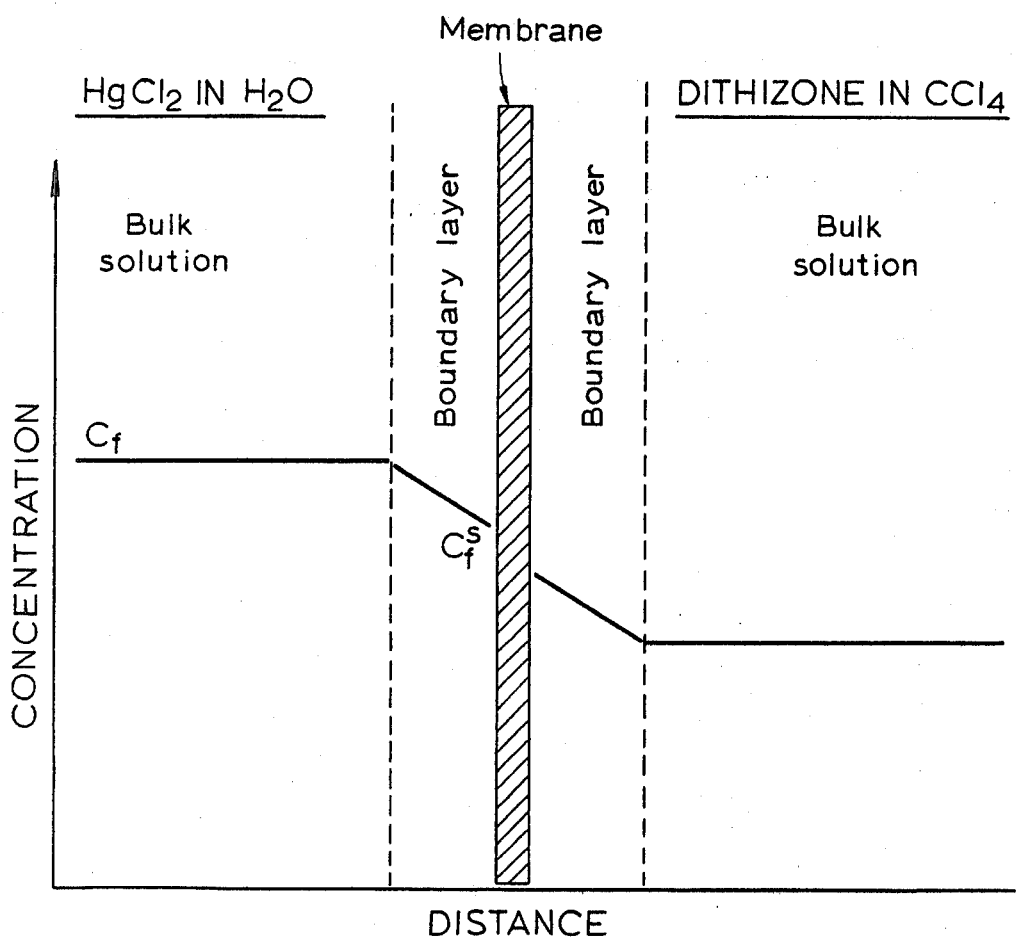

Consider the transfer of $Hg^{2+}$ ions across the polymer membrane under steady state conditions from an aqueous mercuric chloride solution of concentration $C_f$. As a result of transfer of $Hg^{2+}$ ions through the membrane close to the membranes surface on the aqueous side, the fluid will be depleted in $Hg^{2+}$ ions; $(C_f^s)$ will thus be lower than $C_f$. It is assumed that at the aqueous-organic liquid interface, $Hg^{2+}$ ions react instantaneously with dithizone to form mercury dithizonate which is itself very soluble in the organic solvent. However, unless there is very rapid diffusion of the mercury dithizonate away from the aqueous-organic liquid interface into the bulk of the organic liquid, the concentration of mercury dithizonate at the surface of the membrane on the organic-liquid side will be greater than that in the bulk of the organic liquid. Such boundary layers would be sufficient to reduce the transfer rate below what it would be in their absence. The above description is shown diagrammatically in FIG. 4 of the accompanying drawings.

To minimise the effect of boundary layers on membrane permeability (in convential dialysis, for instance), the liquids in contact with the membrane were stirred or forced to flow over the surface of the membrane in order to promote mixing of the boundary layers with bulk solution.

The initial results and conclusions were as follows:

1. Membrane

An initial study was made of the accumulation of the $Hg^{2+}$ ion by dithizone (trapping agent) dissolved in either chloroform or carbon tetrachloride.

Two general types of polymer membranes were studied, viz.

(i) water-swellable polymer membranes with a high degree of swelling in aqueous solution (prepared by us)

(ii) commercially available porous polymer membranes. Some of these, e.g. cellulosic membranes, swell in aqueous media. Others, e.g. polytetrafluoroethylene, have no inherent water uptake; diffusion takes place within solvent held in their pores. The membranes were required to possess the following properties:

(i) High permeability towards metal ions: since transport rate is inversely proportional to membrane thickness, very thin membranes were desirable.

(ii) High mechanical strength and flexibility: a balance was necessary between high strength and low membrane thickness.

(iii) Chemical resistance and non-biodegradability: in particular, resistance to organic solvents such as carbon tetrachloride was needed.

(iv) Consistent transport behaviour: i.e. resistance to fouling.

Other conditions being equal, the diffusion rates were not expected to vary appreciably over the long periods of time (months) of anticipated use. Changes in other stream properties such as pH, temperature, undissolved solids content, etc. were expected to affect diffusive flux only to a marginal extent.

Commercial membranes studied included cellophane (regenerated cellulose), cellulose esters and polytetrafluoroethylene.

The membranes studied included Cupraphane, PTFE and Solvinert membranes as referred to above.

2. Trapping Agent

For the initial laboratory experiments, it was determined that the trapping agent should be highly insoluble in water and in dilute aqueous solutions of inorganic ions, but reasonably soluble in carrier phases such as organic solvents which themselves are insoluble in water or aqueous solutions of inorganic ions. Dithizone possesses these properties. Also, as an analytical reagent for mercury and other metals, dithizone has been studied extensively and much is known about its usefulness and limitations. For these reasons, dithizone was chosen as a trapping agent in preference to one of the newer but incompletely studied reagents.

3. Organic Solvent

The properties of the organic solvent used to dissolve the trapping agent are of major importance. There are two main reasons why the concentration of trapping agent in the organic solvent should be high, viz.

(i) to reduce the volume of the accumulator (an important practical consideration)

(ii) to prevent the trapping agent present in a 'prolonged action' accumulator becoming saturated with trapped metal ions during its life-time. In other words, a large excess of dithizone was used over the concentration required to complex all the metal ions which could be transported to the trapping system (within the specified working life of the accumulator).

Dithizone dissolves in most organic solvents to a greater or lesser extent. In hydrocarbons, it is only very slightly soluble. Its solubility in chloroform at 20° C is about 20 g/l, and in carbon tetrachloride about 0.5 g/l. These two solvents were used in the preparation of the dithizone solutions for the initial tests, but hexane, octane, benzene and toluene were also studied. Chloroform was preferred because of its higher solubility for dithizone. However, one important property, viz. water solubility, governed the usefulness of these organic solvents in the accumulators. The solubilities of chloroform and carbon tetrachloride in water at 20° C are about 8 g/l. and 0.77 g/l, respectively. This tenfold difference in solubility was sufficient to suggest initial use of carbon tetrachloride.

Both chloroform (density = 1.48 at 20° C) and carbon tetrachloride (density = 1.59 at 20° C) are denser than water or dilute aqueous solutions of inorganic salts. Because of this, special care had to be taken when filling the accumulators to prevent leakage of either solvent or aqueous phase through the membrane due to a pressure differential at the membrane.

The solubility of the trapped species, (i.e. mercury dithizonate) should be high enough to prevent its precipitation during the anticipated life-time of the accumulator.

4. Mass Balance

Values of membrane permeability, P, were obtained by measuring the depletion of $Hg^{2+}$ from the aqueous compartment of a glass accumulator. However, since the experiments were done at pH 5.5, it was possible that some $Hg^{2+}$ was adsorbed onto the walls of the aqueous compartment. It was also possible that some mercury in either ionic or organic form was trapped in the membrane. It was therefore necessary to investigate the mass balance which could be represented by:

$$\begin{bmatrix} \text{Loss of Hg}^{2+} \\ \text{from} \\ \text{aqueous solution} \end{bmatrix} = \begin{bmatrix} \text{Hg}^{2+} \text{ adsorbed} \\ \text{on glass} \end{bmatrix} + \quad \text{(i)}$$

$$\begin{bmatrix} Hg^{2+} \text{ trapped} \\ \text{in trapping} \\ \text{compartment} \end{bmatrix} + \begin{bmatrix} Hg \text{ adsorbed} \\ \text{onto} \\ \text{membrane} \end{bmatrix}$$

A - Adsorption of $Hg^{2+}$ onto glass

A first order estimation of the adsorption of $Hg^{2+}$ onto the accumulator walls was obtained by simple experiments in which the depletion of $Hg^{2+}$ from the aqueous compartment of an accumulator whose organic compartment contained carbon tetrachloride but no trapping agent was measured. This system is shown diagrammatically below.

| Aqueous compartment | Organic compartment |
|---|---|
| $HgCl_2$ in water, stirred | $CCl_4$ |
| | Cupraphane membrane |

Tables 1 and 2 below refer respectively to the results of mass balance experiments and of accumulator experiments.

Figure 5:
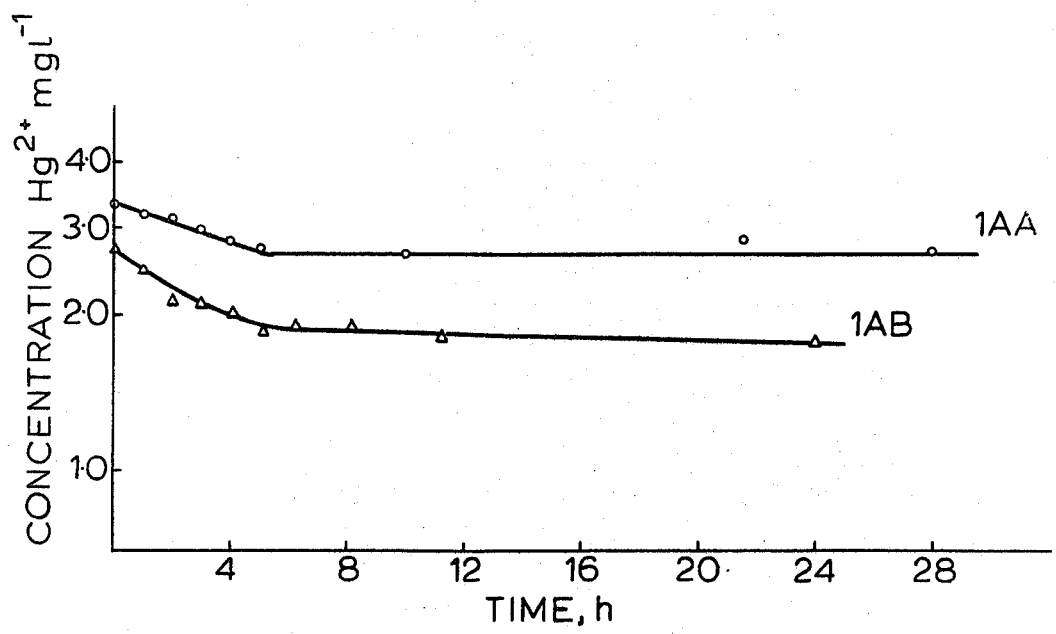
Figure 6:
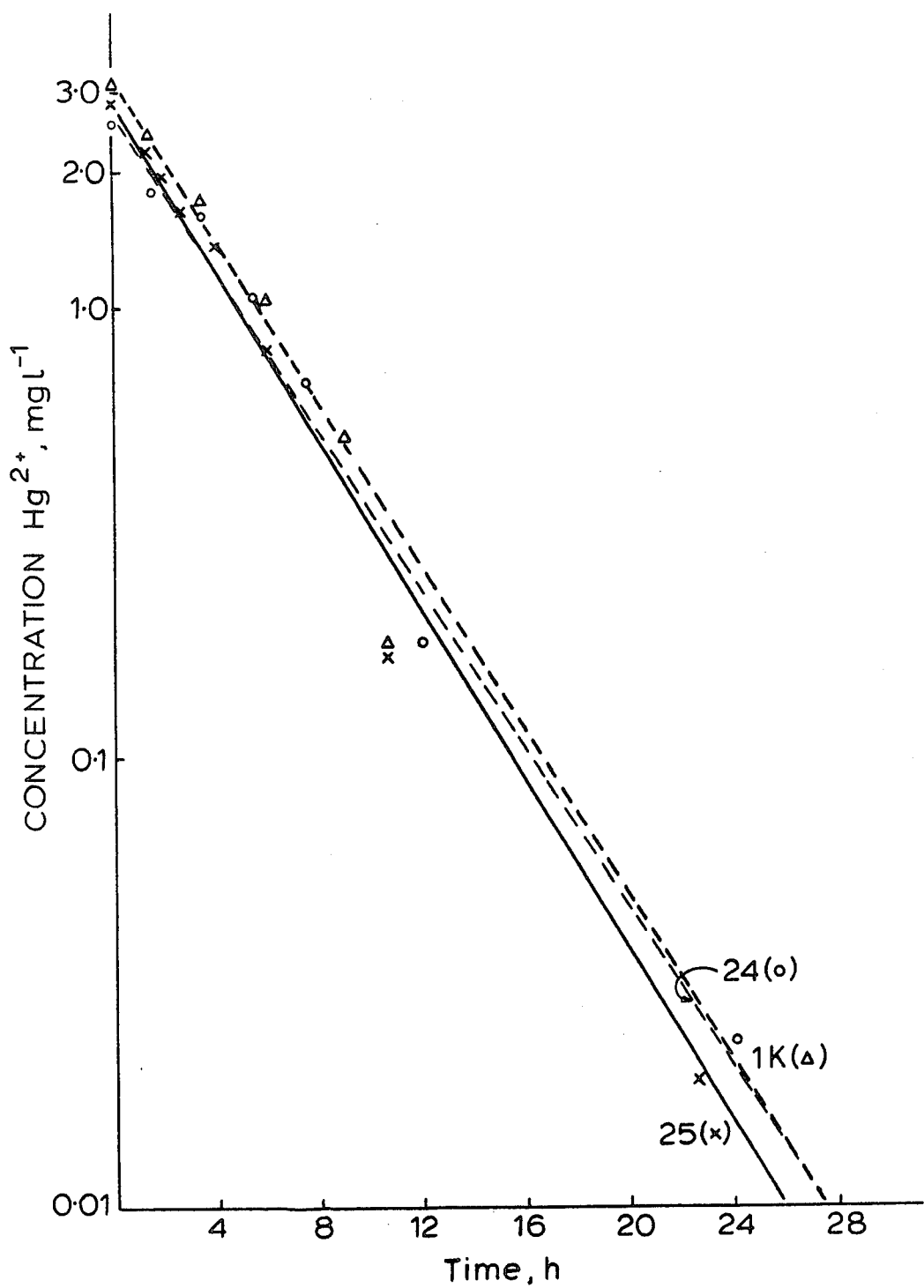
Figure 7:
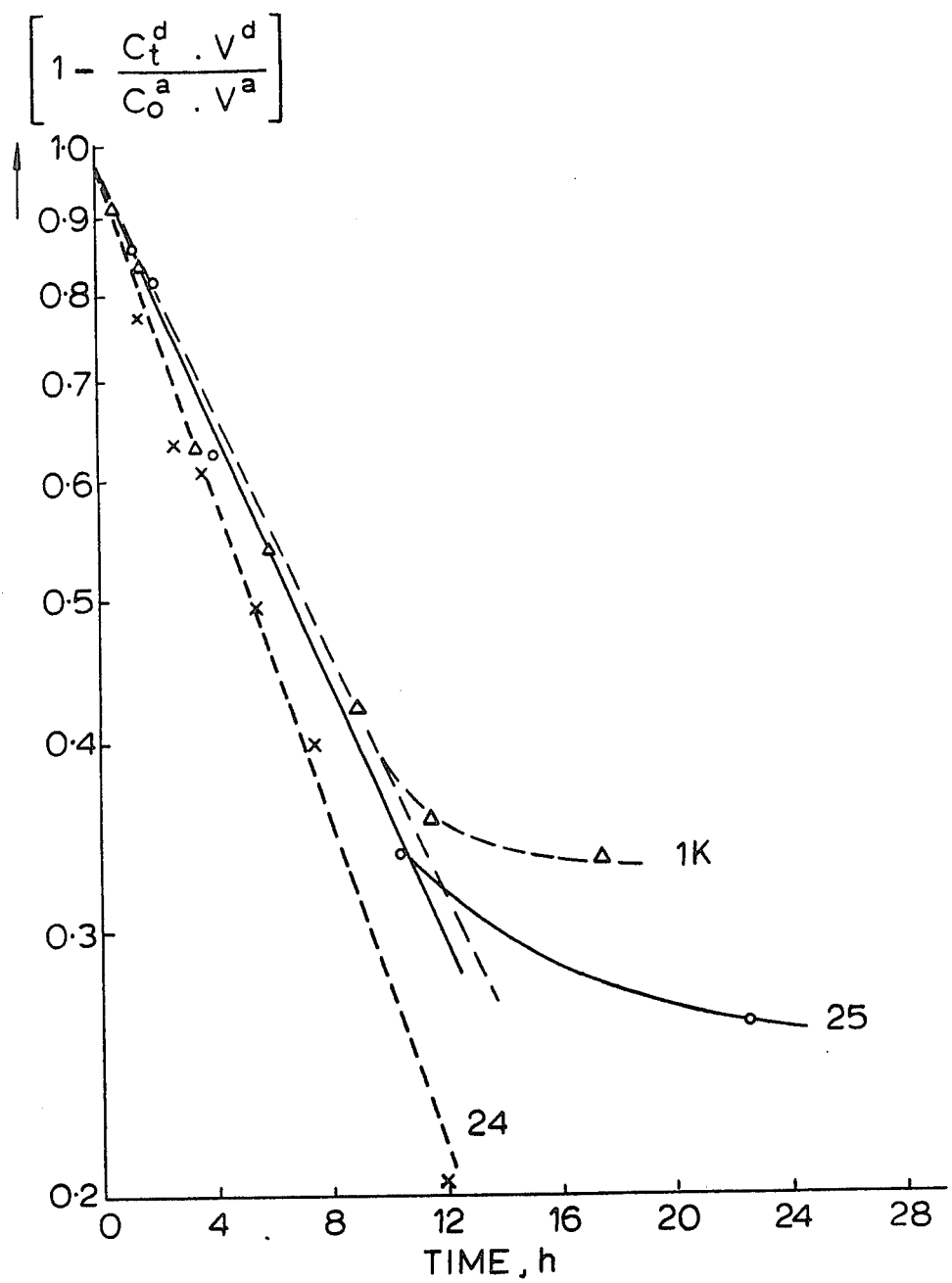

FIGS. 5 and 6 of the accompanying drawings are graphs showing the depletion of $Hg^{2+}$ from an aqueous compartment; and FIG. 7 is a graph showing the accumulation of Hg by dithizone.

hydrochloric acid and stannous chloride) and the concentration of $Hg^{2+}$.

It was assumed that the adsorption was related to concentration by the classical Freundlich adsorption isotherm:

$$x = kC^{1/n} \quad \text{(ix)}$$

where
x = amount $Hg^{2+}$ adsorbed;
C = concentration of $Hg^{2+}$;
k and n = constants; and
$1/n > 1$ Thus, although up to 30% of available $Hg^{2+}$ could apparently be adsorbed onto glass from a solution whose initial $Hg^{2+}$ concentration was 3 mg $l^{-1}$, all available mercury would not be adsorbed from solutions whose initial concentrations were 0.90 mg $l^{-1}$ or less.

Mass balance experiments were done in which both the depletion of $Hg^{2+}$ from the aqueous compartment and the accumulation of Hg in the trapping compartment were determined. At the end of the experiments the membranes were analysed for bound mercury.

Values of membrane permeability, P, were calculated in two ways, viz (a) from the depletion of $Hg^{2+}$ from the aqueous compartment and (b) from the accumulation of Hg by dithizone. The latter method is described below:

Calculation of P from accumulation data: The depletion of $Hg^{2+}$ from the aqueous compartment can be

TABLE 1.

Results of mass balance experiments

| Exp. No. (IRI ref.) | Temp. °C | Accumulator Design Type | Membrane area, cm² | Vol. liquid in Aqueous compart. | Vol. liquid in Trapping compart. | Stirring in Aqueous compart. | Stirring in Trapping compart. | Permeability P, (cm sec⁻¹ × 10⁴) From $Hg^{2+}$ depletion FIG. 5 | From Hg accumulation FIG. 6 | From depletion-adsorption data FIG. 7 | Hg trapped in membrane % of initial conc. |
|---|---|---|---|---|---|---|---|---|---|---|---|
| 1K | 21-22 | 4 | 44 | 400 | 700 | Yes | No | 5.20 | 2.28 | 2.65 | 4.1 |
| 24* | 21-22 | 4 | 44 | 400 | 700 | Yes | No | 5.06 | 3.12 | — | 0.7 |
| 25 | 20-22 | 4 | 44 | 400 | 700 | Yes | No | 5.46 | 2.56 | 2.75 | 1.5 |

NOTE:
(a) Cupraphane membranes
(b) Dithizone conc. = 10 mg $l^{-1}$
(c) Initial $Hg^{2+}$ concentration = 3.06 mg $l^{-1}$ (1K), 2.55 mg $l^{-1}$ (24) and 2.80 mg $l^{-1}$ (25)
*Silanised aqueous compartment.

TABLE 2.

Results of accumulator experiments

| Exp. No. (IRI ref) | Temp. °C | Membrane area cm² | Vol. Liquid in Aqueous Compart. | Vol. Liquid in Trapping Compart. | Stirring in Aqueous Compart. | Stirring in Trapping Compart. | Initial Conc. $Hg^{2+}$ mg $l^{-1}$ | Conc. dithizone mg $l^{-1}$ | Permeability, P cm. sec⁻¹ × 10⁴ |
|---|---|---|---|---|---|---|---|---|---|
| 1AA | 21-22 | 44 | 400 | 700 | Yes | No | 3.15 | 0 | — |
| 1AB | 21-22 | 44 | 400 | 700 | Yes | No | 2.80 | 0 | — |
| 1 D | 20-22 | 44 | 400 | 700 | Yes | No | 3.05 | 10 | 4.15** |
| 22 | 22-23 | 44 | 400 | 700 | Yes | No | 2.80 | 40 | 14.50** |
| 19 | 22-23 | 44 | 400 | 700 | Yes | No | 2.55 | 400 | 23.50** |
| 18 | 22-23 | 44 | 400 | 700 | Yes | No | 2.40 | 500 | 24.10** |
| 23* | 22-23 | 44 | 400 | 700 | Yes | No | 3.00 | 10 | 5.64** |

*pH = 1;
**adsorption effects ignored in calculation

In the experiment to study adsorption of $Hg^{2+}$ onto the walls of the glass vessel it is seen (FIG. 5) that, the $Hg^{2+}$ concentration decreases over a period of time and thereafter remains essentially constant. It is assumed that this decrease in concentration is due solely to adsorption of $Hg^{2+}$ onto the glass walls and the glass stirrer of the accumulator.

The rate and extent of the $Hg^{2+}$ adsorption depended on a number of factors, including the nature of the glass surface (rough or smooth), and the success of previous desorption treatments (all glassware was treated with represented by $$\ln \frac{C_o^a}{C_t^a} = \frac{P.A.t}{V^a} \quad \text{(x)}$$

$$\therefore \ln \frac{C_t^a}{C_o^a} = -\frac{P.A.t}{V^a} \quad \text{(xi)}$$

where $C_o^a$ = initial Hg²⁺ concentration in aqueous compartment $C_t^a$ = Hg²⁺ concentration in aqueous compartment at time t $V^a$ = volume of aqueous compartment A = area of membrane Now $C_o^a V^a = C_t^a V^a + C_t^d V^d$   (xii)

where $C_t^d$ = concentration of Hg trapped in organic compartment $V^d$ = volume of organic compartment $$\therefore 1 = \frac{C_t^a}{C_o^a} + \frac{C_t^d V^d}{C_o^a V^a} \quad \text{(xiii)}$$

$$\text{and } 1 = \exp\left(-\frac{PAt}{V^a}\right) + \frac{C_t^d \cdot V^d}{C_o^a \cdot V^a} \quad \text{(xiv)}$$

$$\ln\left[1 - \frac{C_t^d \cdot V^d}{C_o^a \cdot V^a}\right] = -\frac{PAt}{V^a} \quad \text{(xv)}$$

Thus, a plot of log $$\left[1 - \frac{C_t^d \cdot V^d}{C_o^a \cdot V^a}\right]$$

against t should be a straight line of slope = $-PAt/2.303 V^a$.

Results of the mass balance experiments are given in FIGS. 5 – 7 of the accompanying drawings and in Table 1 (referred to above). The values of P calculated from the depletion of Hg²⁺ from the aqueous compartment (FIG. 6) are greater than those calculated from the accumulation of Hg by dithizone (FIG. 7, P calculated from the linear portion of the graph). This difference is due almost entirely to the adsorption of Hg²⁺ onto the walls of the aqueous compartment. For accurate values, therefore, allowance should be made for this adsorption.

5. The effect of dithizone concentration.

The effect of increasing the concentration of dithizone was investigated. The results are given in Table 2 above. It is seen that increasing the dithizone concentration has a significant effect on the rate of accumulation. In the absence of data from systems with dithizone concentration of between 40 and 400 mg l⁻¹ it appears that above 400 mg l⁻¹ dithizone, the permeability P is essentially independent of dithizone concentration.

6. The effect of pH

An experiment was carried out to investigate the accumulation by dithizone of Hg from aqueous HgCl₂ made acid to pH = 1 with hydrochloric acid. Although pH 1 conditions are unlikely to be met in practice it was thought that this experiment would, in addition to indicating the effect of acid pH, eliminate the adsorption onto glass experienced at pH 5.5 The result is shown in Table 2. The rate of accumulation was somewhat greater than that found at pH 5.5 and could be due to decreased adsorption effects.

7. Simulated river conditions.

Figure 8:
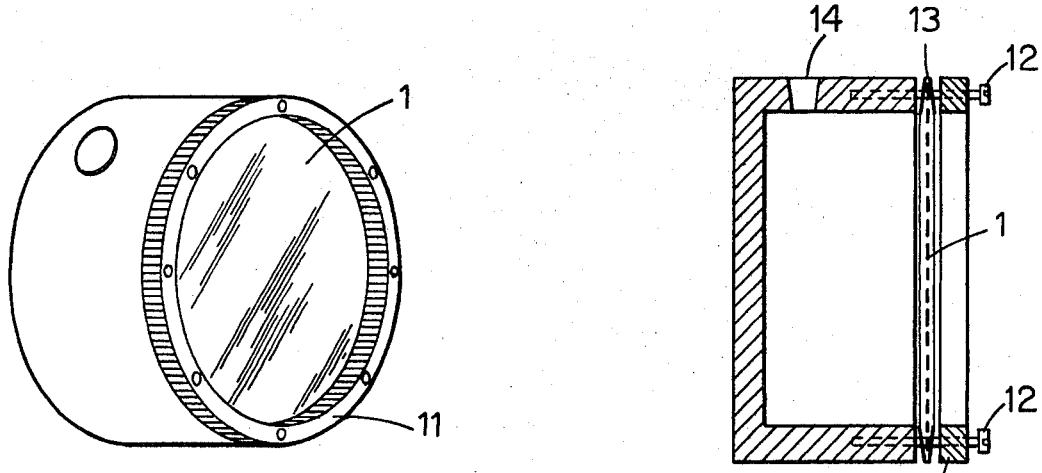

All previous experiments were effected with systems in which the concentration of Hg²⁺ decreased with time. It was decided, therefore, to attempt to simulate the practical situation in which an accumulator is located in a stream with a constant concentration of Hg²⁺. The accumulator used is shown in FIG. 8 of the accompanying drawings. The membrane 1 is held by a polythene flange 11 and retaining screws 12 acting on a polythene gasket 13. An aperture 14 is provided in the body of the accumulator for filling and sampling. The accumulator was milled from block polypropylene. The accumulator which used a cupraphane membrane (a regenerated cellulose membrane) having an area of 113 cm², and 10 mg/l dithizone in carbon tetrachloride, was suspended, with the membrane 1 face up, in the center of a large plastic container filled with 40 liters of HgCl₂ solution. An attempt was made to maintain a constant concentration of Hg²⁺ by adding fresh HgCl₂ solution via a metering pump at a rate equivalent to estimated rate accumulation. The system was stirred by two paddle stirrers located at different depths in the container and the experiment was continued for 19 h during which time the concentration of Hg²⁺ in the aqueous system was measured at intervals. No attempt was made to control temperature which varied between 18° and 21° C during the experiment. At the end of the experiment, the total amount of Hg accumulated was measured.

The results were as follows: (a) The concentrations of Hg²⁺ in the aqueous phase during the experiment were

| Time, h | 0 | 1 | 2 | 3 | 4 | 5 | 6 | 7 |
|---|---|---|---|---|---|---|---|---|
| Hg²⁺, mg l⁻¹ × 10² | 9.2 | 9.2 | 8.5 | 9.0 | 8.4 | 7.9 | 8.1 | 7.9 |

For calculation purposes an average concentration $\bar{C}$, = 0.082 mg l⁻¹ was used.

(b) The estimated rate of accumulation R', is calculated from the equation:

$$R' = P A \bar{C} \quad \text{(xvi)}$$

and therefore depends on the values of P and $\bar{C}$ chosen.

In this experiment, it is not possible to quote an accurate value for P since (i) the flow conditions at the membrane surface cannot be correlated directly with those in the glass accumulator experiments, and the values of P are somewhat high due to adsorption effects. However values of between 1 × 10⁻⁴ and 2 × 10⁻⁴ cm sec⁻¹ for P were thought to be reasonable Using these values, A = 113 cm² and $\bar{C}$ = 0.082 mg l⁻¹, an estimated rate of accumulation of between 8.5 × 10⁻⁷ and 17 × 10⁻⁷ mg sec⁻¹ is obtained.

The total Hg accumulated by the accumulator in 19 h = 55 μg. This gives a rate of accumulation of 8.04 × 10⁻⁷ mg sec⁻¹ (and, substituting into the equation (xvi) in (b) above, a value for P of 0.87 × 10⁻⁴ cm. sec³¹ ¹) The agreement between actual and estimated rates of accumulation was considered reasonably satisfactory.

8. Copper compounds

Experiments were carried out to determine to what extent copper, in the form of the carbonate complex (CuCO₃) or the glycine complex (see M. J. Stiff, Water Research, 5, 1971, 171–176 and 585–589) is accumulated by dithizone. Preliminary results indicated that the accumulation rates for these complexes were of the same order of magnitude as those for Hg²⁺.

9. Synthetic water-swellable polymer membranes

Considerable attention was given to the development of synthetic membranes which swell significantly when in contact with water. Two methods of membrane preparation were studied.

(a) Crosslinked polyvinyl alcohol membranes were prepared by casting thin films (50 to 250 μm wet thickness) from a solution of polyvinyl alcohol (mol. wt. 70,000) and 4% glyoxal, onto polyethylene coated plates, drying, immersing in dilute hydrochloric acid (to catalyse crosslinking), washing and drying.

(b) Polyvinyl pyrrolidone and poly-(2-hydroxyethyl methacrylate) membranes were prepared by irradiating thin films of the corresponding vinyl monomers with gamma rays from a cobalt-60 source.

The membranes prepared were of lower mechanical wet strength than commercially available membranes although preliminary tests indicated that they had at least comparable transport properties to cupraphane membranes. The commercially available membranes were therefore preferred.

10. Hg Analysis

A Analysis of Hg "trapped" in membrane

At the end of each experiment, the membrane was removed from the accumulator, part dried with a stream of hot air, rinsed in distilled water and then completely dried. Pieces of membrane (30–40 mg) were digested in conc. sulphuric acid (2 ml, MAR grade) at 40°–50° C; 2 ml. conc. nitric acid was then added. This solution was then analysed for Hg as described above. Samples of unused membrane were used as controls.

B Analysis of Hg "trapped" by dithizone

Samples (10 ml) of carbon tetrachloride containing dithizone and complexed Hg were removed from the accumulator and evaporated to dryness under a stream of nitrogen. The residues were digested in conc. sulphuric acid and nitric acid as described above and analysed for Hg by the method described above. Dithizone dissolved in carbon tetrachloride was used as a control.

11. Copper and Zinc Accumulation.

The accumulation of copper and zinc in those soluble forms likely to be found in natural waters was investigated.

As reported by Stiff (Water Research, 5, 1971, 585-599), copper present in polluted surface fresh waters may be both associated with suspended solids and in different soluble chemical states. Of the inorganic anionic species likely to be found in polluted fresh waters, only the bicarbonate-carbonate, chloride, cyanide, phosphate, triphosphate and sulphide need be considered in the context of copper complex formation.

The soluble copper carbonate complex ($CuCO_3$) is formed in bicarbonate solution in the pH range of most natural waters. Copper chloride complexes are unlikely to be found in polluted natural fresh waters since their stability constants are too low to permit their formation at the chloride concentrations likely to be found. Copper is precipitated by phosphate and sulphide without the intermediate formation of soluble complexes. Although copper is strongly complexed by triphosphate, this ligand is easily biologically hydrolysed and, since it is derived principally from detergents, is unlikely to be present in sufficient quantities to complex copper significantly. Copper cyanide complexes (e.g. $Cu(CN_2)$) are very stable and easily formed. Anions such as sulphate, nitrate and silicate are non-complexing species.

Humic acids and peptides originating from decomposed vegetation and peptides and aminoacids in sewage discharges can complex copper significantly in some circumstances.

Copper Carbonate Complex

The cupric ion interacts with bicarbonate ion to form the soluble species $CuCO_3$ as follows:

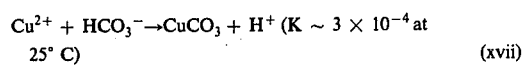

$$Cu^{2+} + HCO_3^- \rightarrow CuCO_3 + H^+ \quad (K \sim 3 \times 10^{-4} \text{ at } 25° C) \qquad \text{(xvii)}$$

The bicarbonate concentrations of most natural waters are within the range of $10^{-3}$ to $5 \times 10^{-3}$M (corresponding to a range of bicarbonate alkalinities of 50-250 mg $l^{-1}$ as $CaCO_3$). The amount of $CuCO_3$ present in such systems is very dependent on pH and, for any stable system, can be calculated from the following equation:

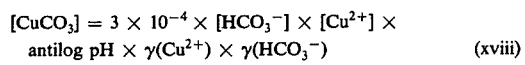

$$[CuCO_3] = 3 \times 10^{-4} \times [HCO_3^-] \times [Cu^{2+}] \times \text{antilog pH} \times \gamma(Cu^{2+}) \times \gamma(HCO_3^-) \qquad \text{(xviii)}$$

At constant pH and bicarbonate concentration, the equilibrium ratio of $Cu^{2+}$ to $CuCO_3$ is constant. The pH range of most natural water is 6 – 8.5, and the equilibrium concentration of $CuCO_3$ increased with increasing pH. In dilute copper solutions ($\sim 1$ mg $l^{-1}$ or less) in $5 \times 10^{-3}$M bicarbonate, nearly all copper is complexed at pH 8 and about 90% copper is complexed at pH 7 but below pH 6, nearly all copper exists as the free cupric ion.

Complexes of Copper wth Aminoacids and Polypeptides

Many natural waters contain polypeptides which result from sewage discharges and from decomposition of vegetable matter. Hydrolysis of polypeptides yields aminoacids. Copper can complex with both polypeptides and aminoacids and significant amounts of these complexes are known to be present in many natural waters. The aminoacid complexes have been more extensively studied and their concentration in many waters ranges from about $10^{-4}$M (in sewage effluent) to about $3 \times 10^{-6}$M (in good quality percolating filter effluent).

Both 1:1 and 1:2 metal-ligand complexes can be formed and data on their stability constants are available (Sillen and Martell, Stability Constants of Metal Ion Complexes, Special Publication No. 17, The Chemical Society, London (1964)).

Many aminoacids complexes are labile and it is therefore difficult accurately to determine their composition in mixed systems although good approximations have been made (Stiff, Water Research, 5, 1971, 585-599). The stability of the complexes increases with increasing pH.

The simplest aminoacid, glycine, is easily biodegradable. Copper-glycine complexes are therefore less likely to be found in polluted waters than copper complexes with other amino acids. However, glycine is a convenient model for laboratory studies and was therefore used. The 1:1 complex is favoured over the 1:2 complex as indicated by their stability constants (log K (1:1 complex) = 8.6; log K (1:2 complex) = 6.9).

Complexes of Copper with Humic Acid

The organic matter of soils and sediments contains amorphous brown to black "colloids" called humic acids, resulting largely from the decomposition of vegetation, which form copper-humic acid complexes.

Not all humic acid substances have the same properties and their chemical compositions are incompletely established although it is well known that they contain phenolic moieties (which can complex with copper) and protein groups (hydrolysed to amino acids which, in turn, complex with copper).

Complexes with Zinc

The stability constants of zinc complexes are similar to those of cadmium complexes. Detailed investigations of the behaviour and properties of cadmium complexes have been reported (Gardiner, WPR Report No. 1273, July 1972). By analogy, the contribution to complexation of zinc by carbonate and aminoacids complexes (at the ligand concentrations likely to be found in natural waters) will be significantly less than in the case of copper (c.f. the logarithms of the stability constants of the 1:1 and 1:2 zinc-glycine complexes are 5.52 and 4.27, respectively).

The following factors were considered and results obtained.

1. Adsorption of metal ions onto glass

The problems of adsorption of metal ions from solutions of pH 5 - 8 onto the glass walls of the accumulator have been referred to above. To minimise adsorption glass vessels were silanised with commercially available reagents.

2. Analysis by atomic absorption spectrophotometry

The analysis of both the aqueous and organic components of the laboratory accumulators was done using acetylene flame atomic absorption spectrophotometry (AAS) according to conventional techniques.

The analysis by AAS was effected with a Varian atomic absorption spectrophotometer, model 1100.

3. Computerisation of results

A computer was programmed to process directly the analytical data obtained by the atomic absorption spectroscopic analysis.

Depletion from Aqueous Compartment

Using analytical data on the amount of metal ion remaining in the aqueous compartment of the accumulator, the computer was programmed to provide:

(a) the gradient of the graph of log C (C = concentration of metal ion remaining in the aqueous compartment) versus time.
(b) the correlation coefficient, r.
(c) the intercept of the log C axis.
(d) the membrane permeability, $P = (P_{aq})$.

Accumulation by Organic Compartment

Using analytical data on the amount of "trapped" metal ion, the computer was programmed to provide:

(a) the gradient of the (linear) graph of $\log (1 - C_t^d V^d / C_o^a V^a)$ versus time.
(b) the correlation coefficient, r.
(c) the membrane permeability, $P = (P_{org})$.

The difference between $P_{aq}$ and $P_{org}$ represents the mass in-balance of the system due to adsorption effects (and possible inaccuracies in analysis).

4. Accumulation experiments

The complete interpretation of results is complicated by the fact that the mode of reaction of $Cu^{2+}$ and $Zn^{2+}$ (and, presumably, their complexes) with dithizone depends to some extent on Ph.

In normal solvent extraction procedures (see Solvent Extraction of Metals, loc. cit.), the primary dithizonate of copper is formed below pH = 7 and the secondary dithizonate is formed above pH 7. Copper is normally quantitatively extracted from aqueous solution at pH 1 - 4, although higher pH values can be used. The preferred extraction pH range for zinc is 5 - 8.

Copper-bicarbonate system

The results of experiments with copper-bicarbonate systems are given in Table 4 below. (Note. Since the bicarbonate concentration and ionic strength of tap water were not measured the values of $[CuCO_3]/[Cu^{2+}]$ may be artificially low).

TABLE 4

Results of accumulator experiments with copper-bicarbonate systems

| IRI Exp. No. | Initial pH | Initial metal ion conc. mg. $l^{-1}$ | Bicarbonate conc. M $\times 10^3$ | $\frac{[CuCO_3]}{[Cu^{2+}]}$ (estimated) | Data from aqueous phase depletion (Log C v. time) | | | Data from organic phase accumulation [$\log (1 - \frac{C_t^d V}{C_o^a V^d})$ v. time] | | |
|---|---|---|---|---|---|---|---|---|---|---|
| | | | | | −gradient $\times 10^4$ | corr. coeff r | $P \times 10^4$, cm.sec$^{-1}$ | −gradient $\times 10^4$ | corr. coeff r | $P \times 10^4$, cm.sec$^{-1}$ |
| 76* | 6.10 | 4.78 | 1 | 0.4 | 0.1089 | −0.8805 | 1.0 (4.1)** | 0.1232 | −0.9257 | 0.5 |
| 59 | 6.61 | 2.83 | 1 | 1.3 | 1.4046 | −0.9954 | 12.4 | 0.4489 | −0.9908 | 4.0 |
| 58 | 6.61 | 2.81 | 1 | 1.3 | 0.8239 | −0.9366 | 7.1 | 0.2186 | −0.7435 | 1.8 |
| 77* | 6.68 | 4.71 | 1 | 1.5 | 0.1179 | −0.9086 | 1.0 (5.3)** | 0.0658 | −0.9953 | 0.6 |
| 63 | 6.81 | 4.68 | 1 | 2.1 | 0.9871 | −0.9046 | 7.4 | 0.4961 | −0.9976 | 4.0 |
| 38 | 6.90 | 2.26 | 1 | 2.5 | 1.2827 | −0.9735 | 10.8 | — | — | — |
| 37 | 6.90 | 3.32 | 1 | 2.5 | 1.1392 | −0.9790 | 10.1 | — | — | — |
| 54 | 7.00 | 4.58 | 2 | 6.3 | 0.8468 | −0.9814 | 7.3 | 0.1174 | −0.9399 | 1.0 |
| 55 | 7.00 | 4.40 | 2 | 6.3 | 0.8855 | −0.9812 | 8.9 | 0.2723 | −0.9767 | 2.4 |
| 64 | 7.01 | 4.68 | 5 | 16.2 | 0.1402 | −0.9001 | 1.7 (5.4)** | 0.2030 | −0.9526 | 1.8 |
| 65 | 7.01 | 4.50 | 5 | 16.2 | 0.1693 | −0.8806 | 1.5 | 0.2710 | −0.9391 | 2.3 |

TABLE 4-continued
Results of accumulator experiments with copper-bicarbonate systems

| IRI Exp. No. | Initial pH | Initial metal ion conc. mg. l$^{-1}$ | Bicarbonate conc. M × 10$^3$ | $\frac{[CuCO_3]}{[Cu^{2+}]}$ (estimated) | Data from aqueous phase depletion (Log C v. time) | | | Data from organic phase accumulation[log $(1 - \frac{C_i^d V}{C_o^a V^d})$ v. time] | | |
|---|---|---|---|---|---|---|---|---|---|---|
| | | | | | −gradient × 10$^4$ | corr. coeff r | P × 10$^4$, cm.sec$^{-1}$ | −gradient × 10$^4$ | corr. coeff r | P × 10$^4$, cm.sec$^{-1}$ |
| | | | | | | | (6.9)** | | | |

*All dilutions with tap water (bicarbonate concentration of tap water ignored in all calculations in this report)
**Data in brackets obtained from initial linear part of curved plot.
Effects due to adsorption ignored in all calculation of P in this report.

Examination of results obtained from experiments within the pH range 6.6 to 7.0 and bicarbonate concentration $1 \times 10^{-3}$M indicated a probable inverse relationship between P and the initial copper concentration (and, by calculation, the free cupric ion concentration). It was forecast that the dependence of P on metal-ion concentration would not be significant in natural systems containing lower concentrations of metal ion than used in this laboratory study.

It will also be seen (c.f. Experiments Nos. 37, 55 and 64) that P decreases with an increase in the ratio [CuCO$_3$]/[Cu$^{2+}$] which, in this case, is also accompanied by a decrease in the amount of free cupric ion.

Figure 9:
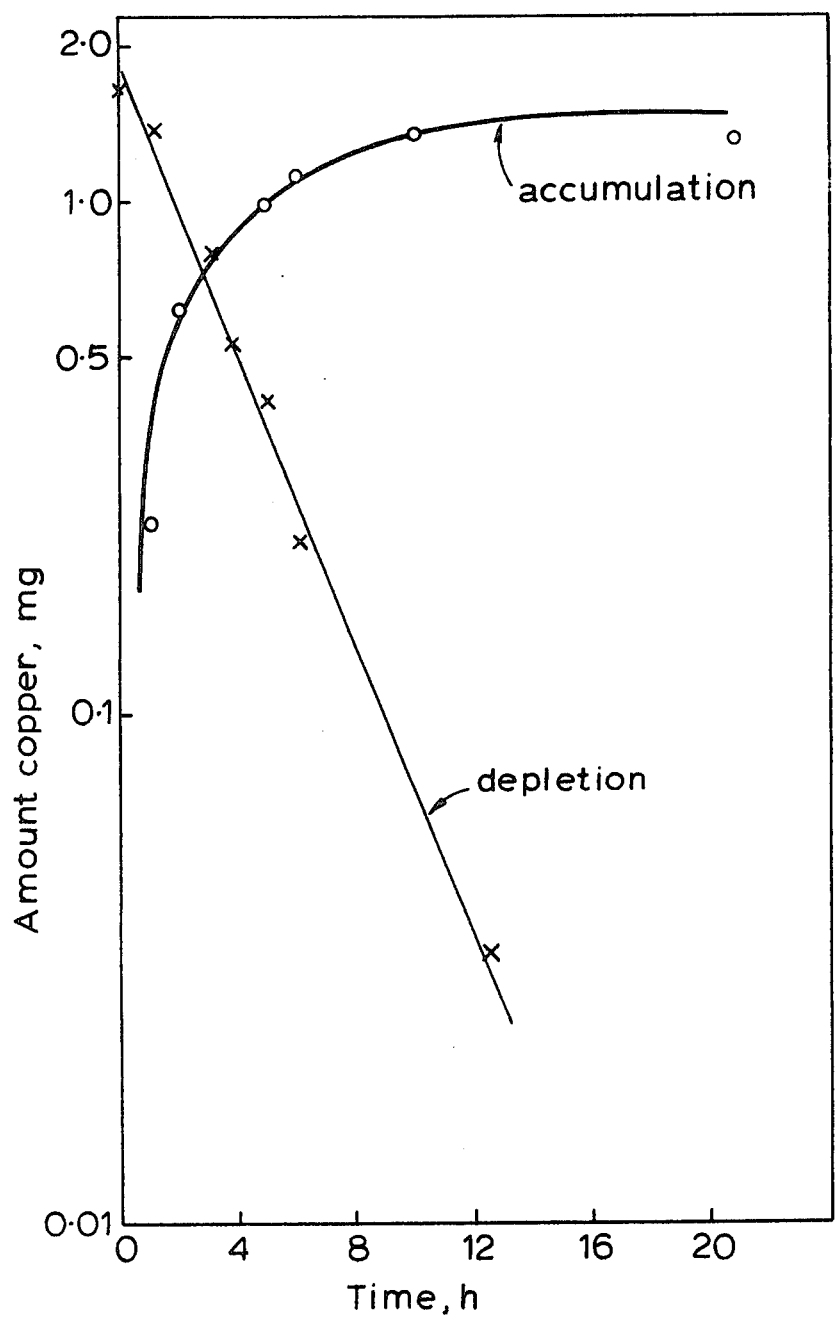
Figure 10:
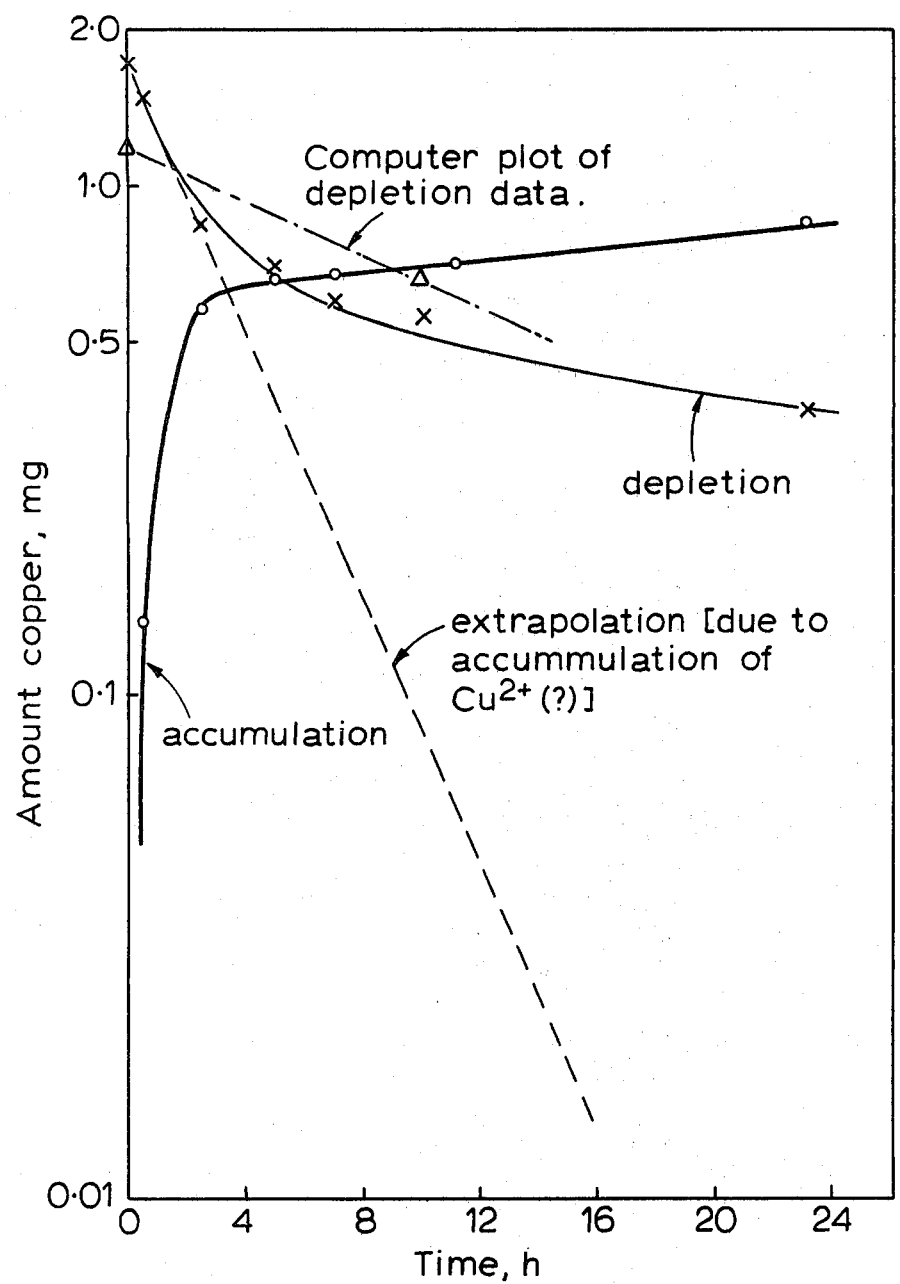

The interpretation of the results is complicated by differences in the shapes of the graphical presentation of the data. The plots of log (amount copper remaining in aqueous phase) versus time were linear for Experiments Nos. 59, 58, 63, 38, 37, 54 and 55 (see e.g. FIG. 9 of the accompanying drawings) but curved for experiments 76, 77, 64 and 65 (see e.g. FIG. 10 of the drawings).

Values of P ($P_{aq}$) obtained from linear plots were of the same order (7–12 × 10$^{-4}$cm. sec$^{-1}$). It is not known with certainty whether these linear plots represent accumulation of Cu$^{2+}$ and CuCO$_3$ or just Cu$^{2+}$. Since CuCO$_3$ is a labile complex, removal of Cu$^{2+}$ from a Cu$^{2+}$ - CuCO$_3$ system will, by the law of mass action, cause dissociation of CuCO$_3$. If the rate of reaction of Cu$^{2+}$ with dithizone is similar to the rate of dissociation of CuCO$_3$, complete dissociation of CuCO$_3$ will soon occur.

Values of P obtained from the curved plots (using the computer to draw the best straight line) were lower (1–1.7 × 10$^{-4}$ cm sec$^{-1}$) indicated lower overall accumulation at higher pH values.

It is possible that the curve represents two reactions. The initial part of the curve can be considered to be reasonably linear; if this portion is extrapolated to the time axis (FIG. 10), the value of P so obtained approaches those values obtained from experiments at lower pH and/or bicarbonate concentration. It is suggested that this "linear" part of the curved plot could represent the accumulation of free cupric ion. The curved part of the graph could represent either (a) slower reaction of CuCO$_3$ with dithizone, (b) accumulation of Cu$^{2+}$ resulting from dissociation of CuCO$_3$ or (c) a pH dependent reaction of either Cu$^{2+}$ and/or CuCO$_3$ with dithizone, e.g. the formation of the secondary dithizonate.

Reasons for the differences in the values of P determined from the depletion of the aqueous phase and accumulation by the organic phase have been considered in detail but are omitted here for the sake of brevity. The fact that the values of P did not vary by more than an order of magnitude indicated that the accumulator would be of practical use for monitoring copper in the field.

Copper-glycine systems

Results of experiments with copper-glycine systems are given in Table 5 below. Conditions were chosen so that the systems under study contained more copper-glycine complex than free cupric ion. As with the copper-bicarconate system, there was some evidence that P increased with a decrease in initial copper concentration.

TABLE 5
Results of accumulator experiments with copper-glycine systems

| IRI Exp. No. | Initial pH | Initial metal ion conc. mg. l$^{-1}$ | Glycine conc. M × 10$^3$ | $\frac{[CuL^+]}{[Cu^{2+}]}$ (estimated) | Data from aqueous phase depletion (log C v. time) | | | Data from organic phase accumulation[log $(1 - \frac{C_i^d V}{C_o^a V^d})$ v. time] | | |
|---|---|---|---|---|---|---|---|---|---|---|
| | | | | | −gradient × 10$^4$ | corr. coeff r | P × 10$^4$, cm.sec$^{-1}$ | −gradient × 10$^4$ | corr. coeff r | P × 10$^3$, cm.sec$^{-1}$ |
| 33 | 4.50 | 4.93 | 1 | 1.7 | 0.9589 | −0.9752 | 8.2 | 0.7097 | −0.9744 | 6.0 |
| 34 | 4.50 | 4.83 | 1 | 1.7 | 1.0182 | −0.9956 | 8.8 | 1.0206 | −0.9850 | 8.8 |
| 66 | 4.64 | 2.56 | 1 | 2.2 | 1.9418 | −0.9832 | 14.5 | 0.9558 | −0.9934 | 7.2 |
| 67 | 4.64 | 2.56 | 1 | 2.2 | 1.3328 | −0.9796 | 11.5 | 0.7594 | −0.9862 | 6.4 |
| 74 | 5.42 | 2.88 | 5 | 66.0 | 1.8966 | −0.9833 | 15.6 | 0.9241 | −0.9906 | 7.6 |
| 75 | 5.42 | 4.48 | 5 | 66.0 | 1.0653 | −0.9680 | 9.2 | 0.5754 | −0.9988 | 5.0 |
| 68 | 5.53 | 2.83 | 5 | 98.0 | 2.2562 | −0.9798 | 17.5 | 1.4300 | −0.9917 | 11.1 |
| 69 | 5.53 | 4.76 | 5 | 98.0 | 1.1825 | −0.9648 | 10.2 | 0.5358 | −0.9885 | 4.7 |
| 78* | 7.95 | 5.16 | 5 | 2.2 × 10$^4$ | 0.1055 | −0.9627 | 0.9 (3.8)** | 0.0415 | −0.9608 | 0.4 |
| 79* | 6.93 | 5.16 | 5 | 2.1 × 10$^3$ | 0.1461 | −0.9596 | 0.9** (3.6) | 0.6659 | −0.9129 | 0.6 |

*All dilutions made with tap water (bicarbonate concentration of tap water ignored)
**Data in brackets obtained from linear part of curved plot.
NOTE: L = glycine liquid.

Figure 11:
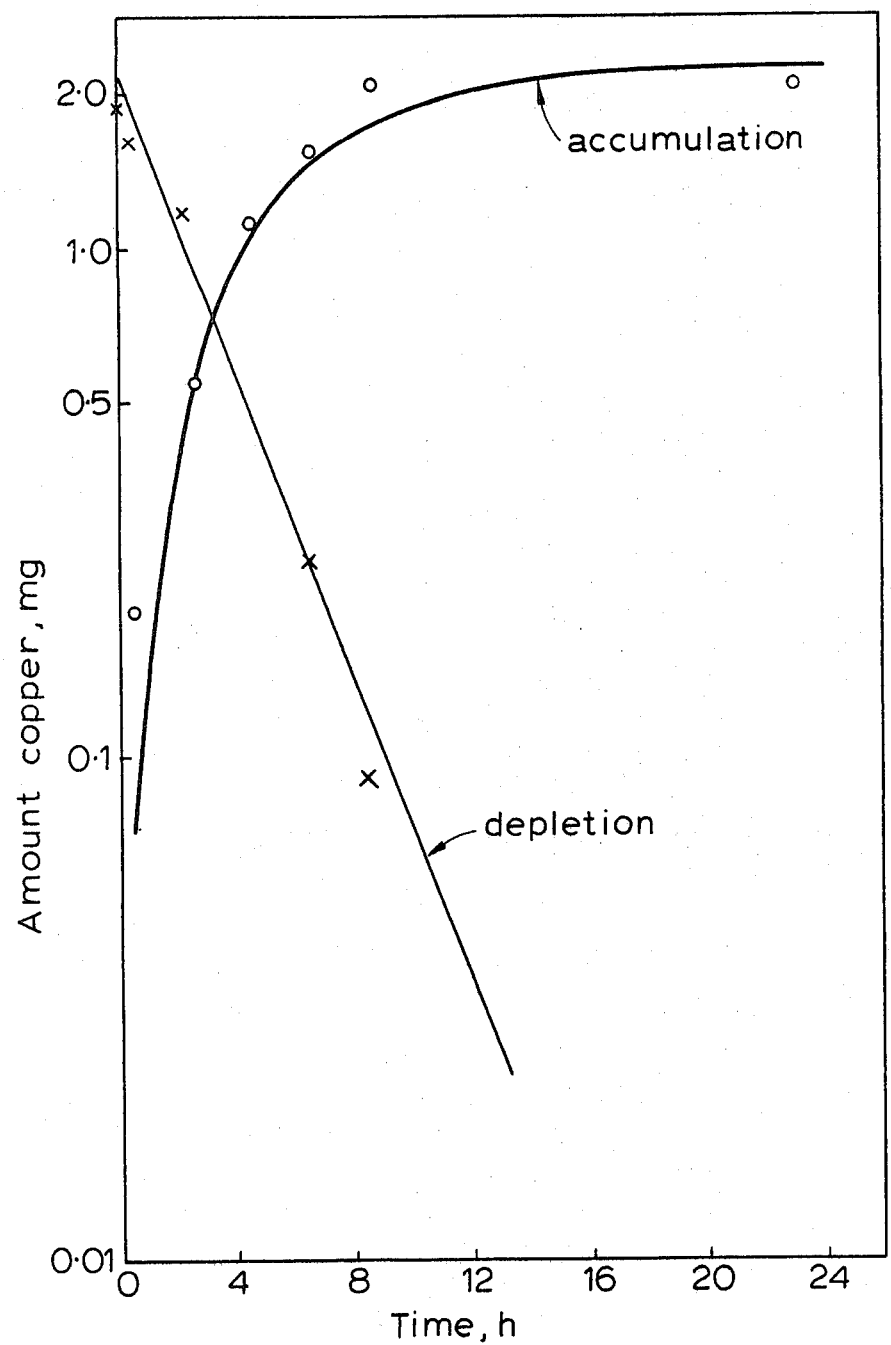
Figure 12:
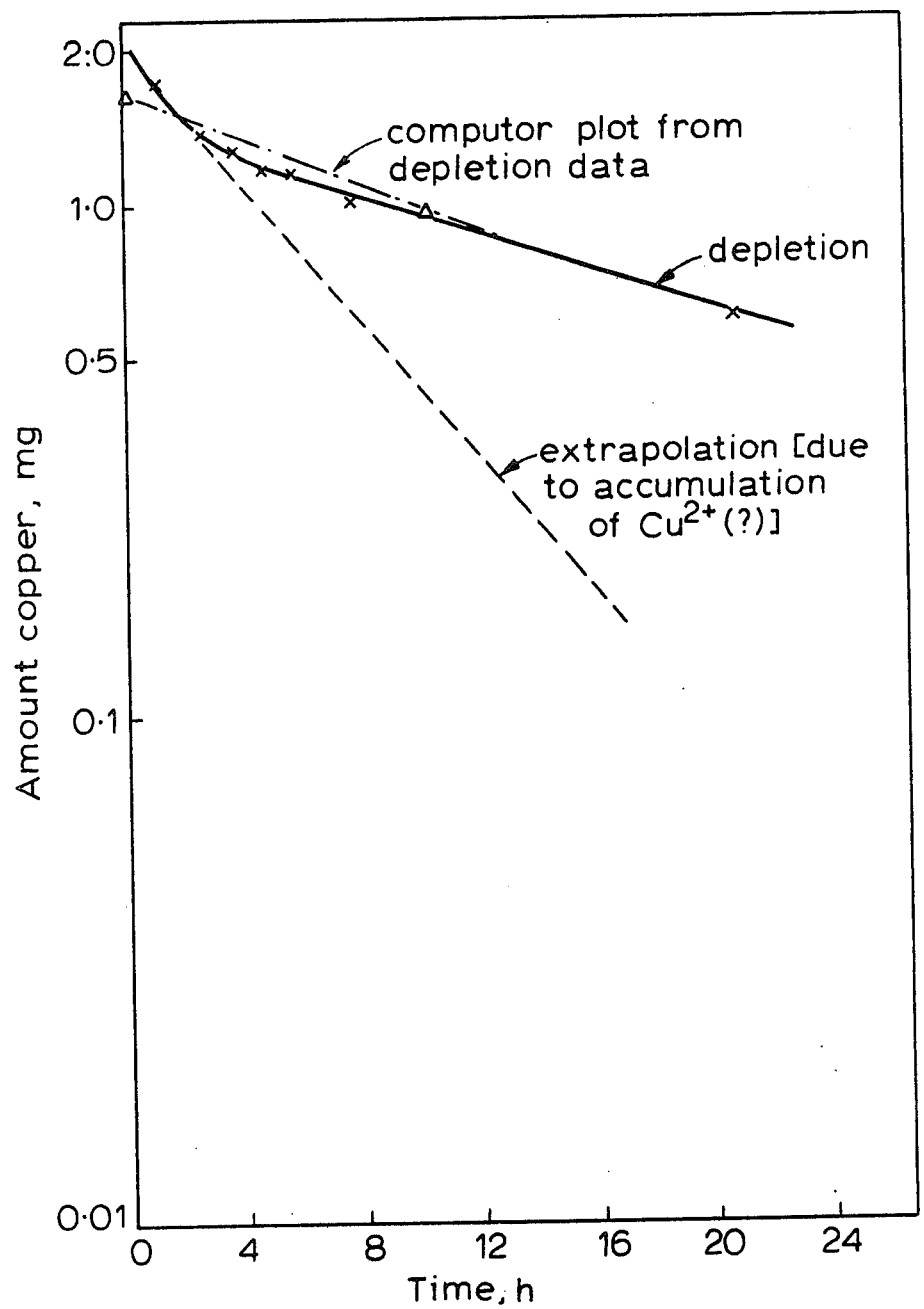

With the exception of Experiments Nos. 78 and 79, the plots of log (amount copper remaining in aqueous phase) versus time were reasonably linear (e.g. FIG. 11 of the drawings). Plots corresponding to Experiments Nos. 78 and 79 (i.e. systems containing nearly 100% copper-glycine complex) were initially curved and then linear (see, e.g., FIG. 12 of the drawings. Although similar explanations to those advanced for the copper-bicarbonate system might have applied here, it was felt more likely, in view of the very large amount of CuL+, that the results represented a slower reaction of CuL+ with dithizone. The accumulaion rate was, nevertheless, significant.

The magnitude of the difference in values of P determined from depletion or accumulation data was similar to that observed with mercuric chloride systems.

Zinc-bicarbonate systems

Results of experiments with zinc-bicarbonate systems are given in Table 6 below.

Figure 13:
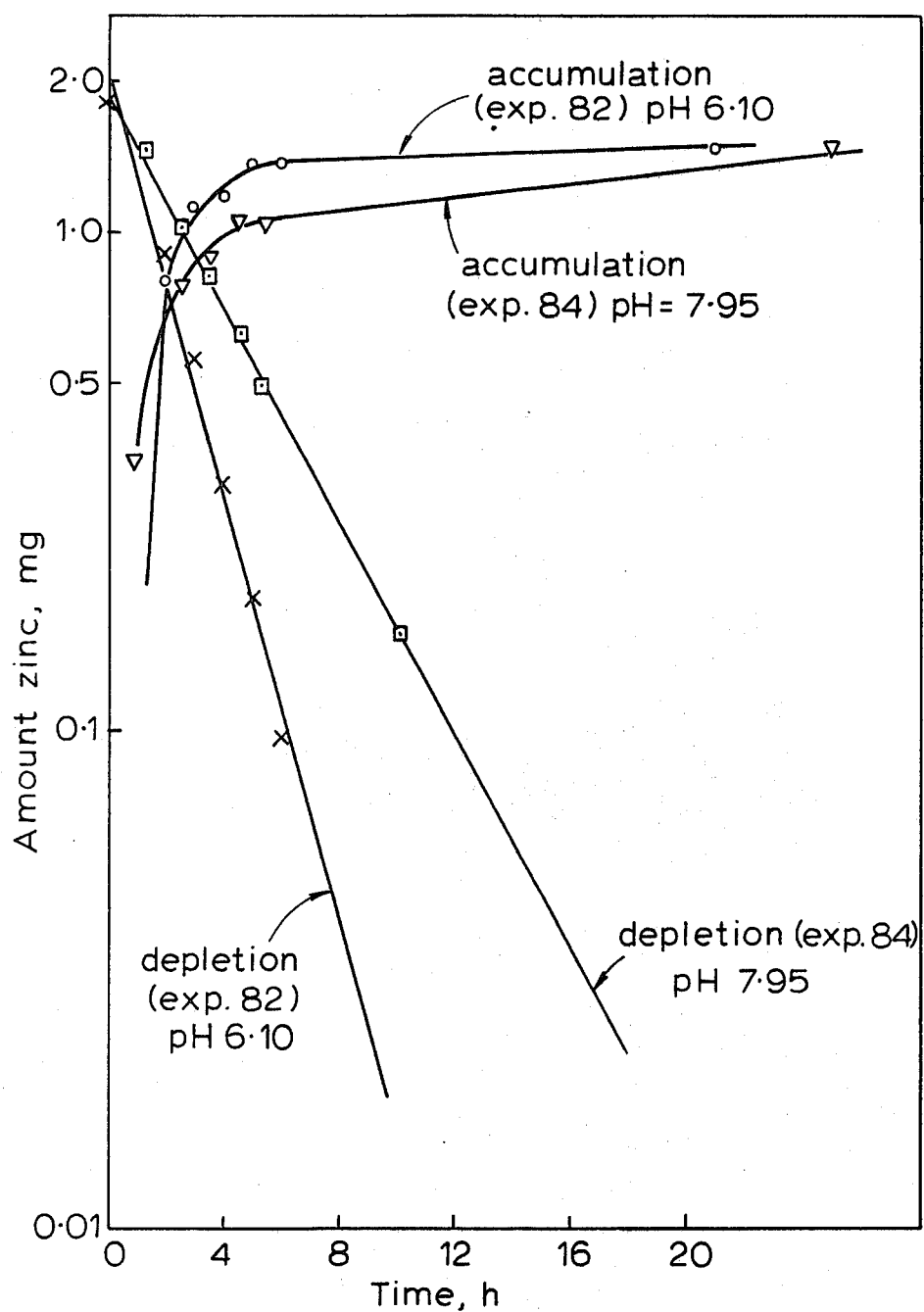

The plots of log (amount zinc remaining in aqueous phase) versus time were linear (see, e.g., FIG. 13), even at pH 7.95 (c.f. behaviour of copper-bicarbonate at pH 7.01). The values of P decreased slightly with increases in pH and $[ZnCO_3]/[Zn^{2+}]$ ratio, but were generally similar to those values found for copper systems at pH < 7.

Zinc-glycine systems

Figure 14:
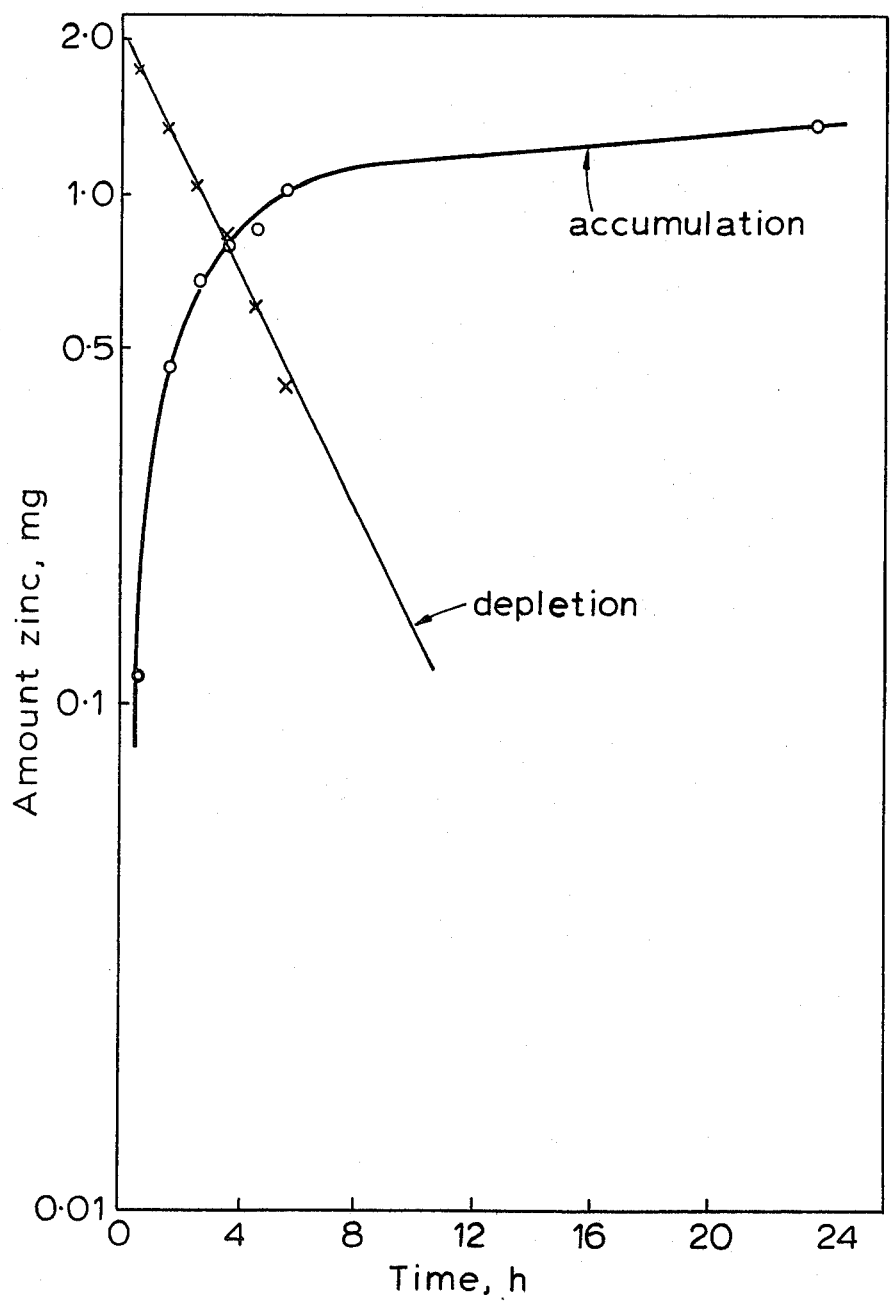

Results of experiments with zinc glycine are given in Table 7 (below) and FIG. 14. Again, the plots of log (amount zinc remaining in aqueous phase) were linear indicating significant reaction of $ZnL^+$ with dithizone.

copper-humic acid complex was too stable for accumulation to occur at normal rates.

5. Alternative trapping agents

The initial field trials were conducted with accumulators containing dithizone as trapping agent.

Dithizone is attractive in that it will complex under the correct conditions with those toxic metal ions (Hg, Cu, Zn, Pb and Cd) of particular interest. As yet no particular problems in the use of dithizone have been found. Nevertheless at the early stage of the project it was considered prudent to identify other trapping agents which might be used if subsequent laboratory studies or field trials did reveal problem areas.

A detailed study was made to locate useful trapping agents for some or all of the toxic metals of interest. The main criteria for the selection of a trapping agent were that:

(a) a high solubility of the trapping agent in carbon tetrachloride or chloroform.

(b) a low solubility of the trapping agent in water.

(c) a high solubility of the metal complex, once formed, in the organic solvent (or liquid medium).

Table 8 below gives relevant information on six reagents and for comparison, dithizone, which is the pre-

TABLE 6

Results of accumulation experiments with zinc-water and zinc-bicarbonate systems

| IRI Exp. No. | Initial pH | Initial metal ion conc. mg. $l^{-1}$ | Bicarbonate conc. $M \times 10^3$ | $[ZnCO_3]/[Zn^{2+}]$ (estimated) | Data from aqueous phase depletion (log C v. time) | | | Data from organic phase accumulation[log $(1 - \frac{C_t^d V^d}{C_o^a V^d})$ v. time] | | |
|---|---|---|---|---|---|---|---|---|---|---|
| | | | | | −gradient $\times 10^4$ | corr. coeff r | $P \times 10^4$, cm.sec$^{-1}$ | −gradient $\times 10^4$ | corr. coeff r | $P \times 10^4$, cm.sec$^{-1}$ |
| 80 | 6.15 | 5.0 | distilled water | All $Zn^{2+}$ | 0.7435 | −0.9796 | 6.3 | 0.5423 | −0.9937 | 4.6 |
| 82* | 6.10 | 5.0 | 5 | 0.05 | 1.3738 | −0.9934 | 11.0 | 0.7332 | −0.9841 | 6.2 |
| 83* | 6.95 | 4.99 | 5 | 0.35 | 1.0317 | −0.9953 | 8.0 | 0.5502 | −0.9989 | 4.9 |
| 45* | 7.10 | 4.88 | 1 | 0.10 | 0.8788 | −0.8540 | 7.8 | — | — | — |
| 84* | 7.95 | 4.96 | 5 | 3.50 | 0.6943 | −0.9987 | 6.0 | 0.5580 | −0.9933 | 4.8 |

*All dilutions done with tap water (bicarbonate concentration of tap water ignored)

TABLE 7

Results of experiments with zinc-glycine systems

| IRI Exp. No. | Initial pH | Initial metal ion conc. mg. $l^{-1}$ | Glycine conc. $M \times 10^3$ | $[ZnL^+]/[Zn^{2+}]$ (estimated) | Data from aqueous phase depletion (log C v. time) | | | Data from organic phase accumulation[log $(1 - \frac{C_t^d V^d}{C_o^a V^d})$ v. time] | | |
|---|---|---|---|---|---|---|---|---|---|---|
| | | | | | −gradient $\times 10^4$ | corr. coeff r | $P \times 10^4$, cm.sec$^{-1}$ | −gradient $\times 10^4$ | corr. coeff r | $P \times 10^4$, cm.sec$^{-1}$ |
| 50 | ~5.5 | 4.72 | 1 | 0.013 | 1.0702 | −0.9981 | 9.0 | — | — | — |
| 51 | ~5.5 | 4.50 | 1 | 0.013 | 0.6884 | −0.9961 | 6.1 | — | — | — |
| 52 | ~5.5 | 4.60 | 1 | 0.013 | 0.5909 | −0.9982 | 5.0 | — | — | — |
| 53 | ~5.5 | 4.50 | 1 | 0.013 | 0.5192 | −0.9981 | 4.3 | — | — | — |
| 48 | 4.7 | 4.98 | 1 | 0.002 | 1.2211 | −0.9963 | 10.5 | — | — | — |
| 85* | 8.0 | 4.95 | 5 | 20.0 | 0.5402 | −0.9993 | 4.6 | 0.3451 | −0.9855 | 3.1 |
| 81* | 8.15 | 5.00 | 5 | 28.0 | 0.7523 | −0.9971 | 6.7 | 0.4163 | −0.9949 | 3.7 |

*All dilutions done with tap water (bicarbonate concentrations of tap water ignored in calculations)

Copper-humic acid system

Only two duplicate experiments were done with the copper humic acid sytem. In both cases, copper could not be detected in the organic phase, indicating that the ferred trapping agent. Although the six trapping agents had higher solubilities with dithizone in carbon tetrachloride, only dibenzoyl methane exhibited a very low water solubility and a very high solubility in carbon tetrachloride. Therefore, dibenzoyl methane was the second trapping agent of choice.

TABLE 8

| | Reagent | Solubility in $H_2O$ | Solubility in $CCl_4$ | Reaction conditions | Solubility of Complex in $CCl_4$ |
|---|---|---|---|---|---|
| 1. | Benzoyl acetone | 384 mg $l^{-1}$ | 304 g $l^{-1}$ | pH 4 – 9 (Cu) pH 5 – 10 (Hg) | Yes |
| 2. | Dibenzoyl methane | $1.34 \times 10^{-3}$ mg $l^{-1}$ | 290 g $l^{-1}$ | pH 4 – 9 (Cu, Fe) slow complexing of Hg at 5.5 – 7.5 | Yes |
| 3. | Dithizone | $5.12 \times 10^{-2}$ mg $l^{-1}$ | 0.5 g $l^{-1}$ | | Yes variable |

TABLE 8-continued

| | Reagent | Solubility in $H_2O$ | Solubility in $CCl_4$ | Reaction conditions | Solubility of Complex in $CCl_4$ |
|---|---|---|---|---|---|
| 4. | Diethylammonium-dithiocarbamate | yes (under certain conditions) no figure available | thought to be excess of 1 g $l^{-1}$ | pH 12 (Cu,Hg) | Yes |
| 5. | 8-hydroxyquinoline | 870 mg $l^{-1}$ | ~100 g $l^{-1}$ in $CHCl_3$ | pH 2 – 12 (Cu) pH 3 (Hg) | Yes |
| 6. | 2 nitroso-1-naphthol | ~2 mg $l^{-1}$ | ~170 g $l^{-1}$ in $CHCl_3$ | | Yes |
| 7. | 2-thenoyl-trifluoroacetone | sparingly | thought to be excess of 1 g $l^{-1}$ | quantitative at pH = 3.6 Concentration must exceed 0.1 M for fast reaction | Yes |

The results of an investigation to determine the ability of dibenzoyl methane to accumulate copper ion are given in Table 9 below. Significant accumulation of copper occurred.

the membrane and surface of the organic liquid. Attempts to identify the reason for this phenomenon were unsuccessful.

TABLE 9.

Results of experiments with copper-bicarbonate systems using dibenzylmethane as trapping agent.

| IRI Exp. No. | Initial pH | Initial metal ion conc. mg. $l^{-1}$ | Bicarbonate conc. M × $10^3$ | $\frac{[CuCo_3]}{[Cu^{2+}]}$ estimated | Data from aqueous phase depletion (log C v. time) | | |
|---|---|---|---|---|---|---|---|
| | | | | | – gradient × $10^4$ | corr. coeff r | P × $10^4$ cm $sec^{-1}$ |
| 41 | ~5.5 | 4.70 | 5 | 0.5 | 0.3762 | −0.9512 | 3.41 |

Concentration dibenzoylmethane in $CCl_4$ = $1gl^{-1}$

6. SIMULATED RIVER CONDITIONS

Figure 15:
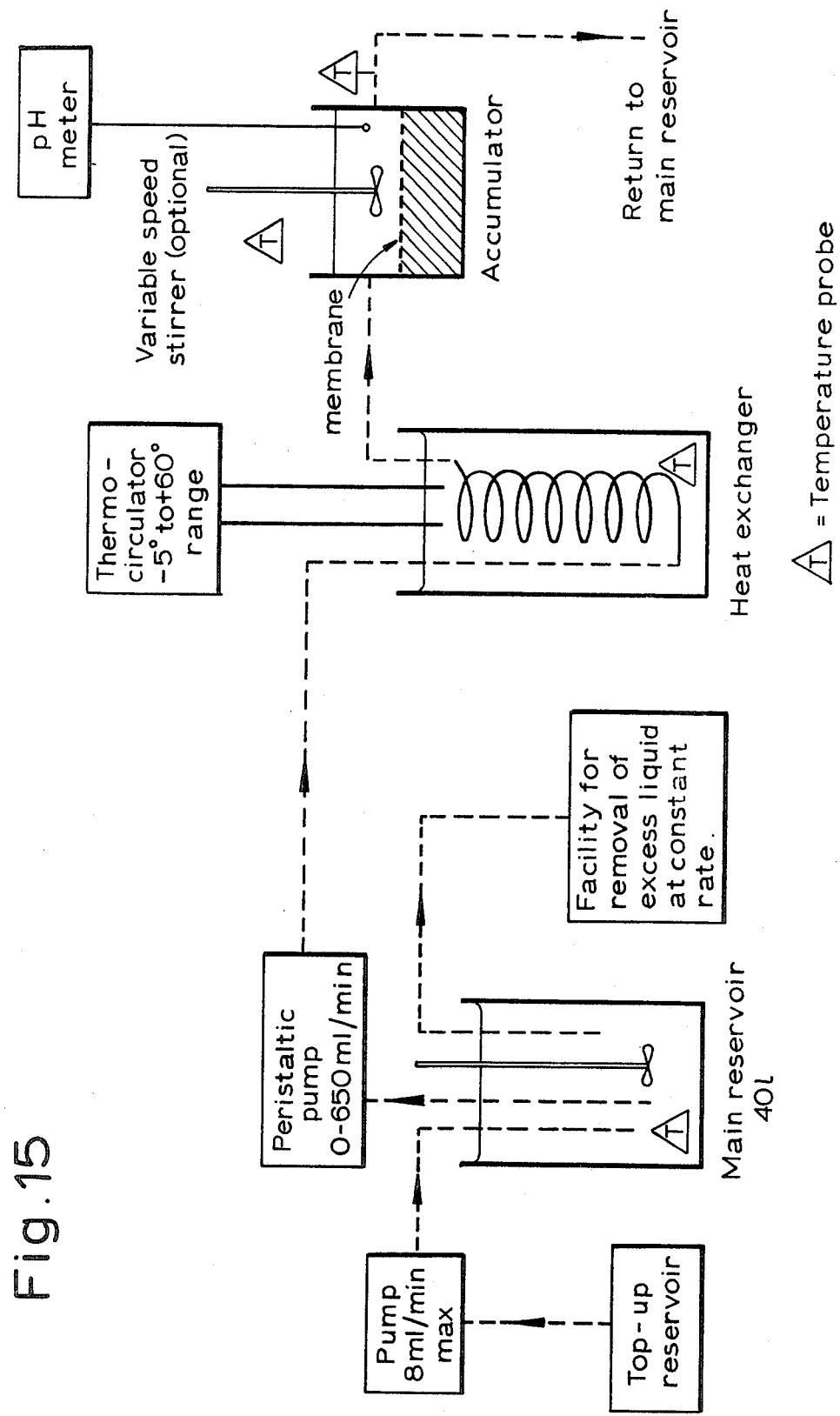

The basic system is shown in FIG. 15 of the accompanying drawings and included facilities for (a) maintaining substantially constant temperature (±0.5° C) over the range −5° to 60° C (for our purposes a temperature range of +5° to +30° C was considered realistic); (b) varying the bulk stream flow (by means of a 0–650 ml $min^{-1}$ peristaltic pump), and (c) varying the flow pattern at the membrane surface (initially simply by means of a variable speed stirrer but later, optionally, by altering the geometry of the cell). A relatively constant concentration of metal ion was achieved by adding fresh metal ion at a rate equivalent to the estimated accumulation rate.

During an initial experiment to investigate the accumulation of cupric ion over a period of several days, a number of problems concerning accumulator design became apparent.

The main problems concerning the accumulator were: (a) its ease of assembly, (b) the tendency to break at certain 'pressure points' during assembly, and (c) the appearance of an air bubble during operation.

Thus, in the plastic accumulator of FIG. 8 the use of a number of tightening screws was a tedious process (unsuitable in the field), there was a tendency to nip the membrane edges during assembly, their proximity to a metal ion accumulating system was obviously undesirable (this difficulty was met by PTFE coating.

Figure 16:
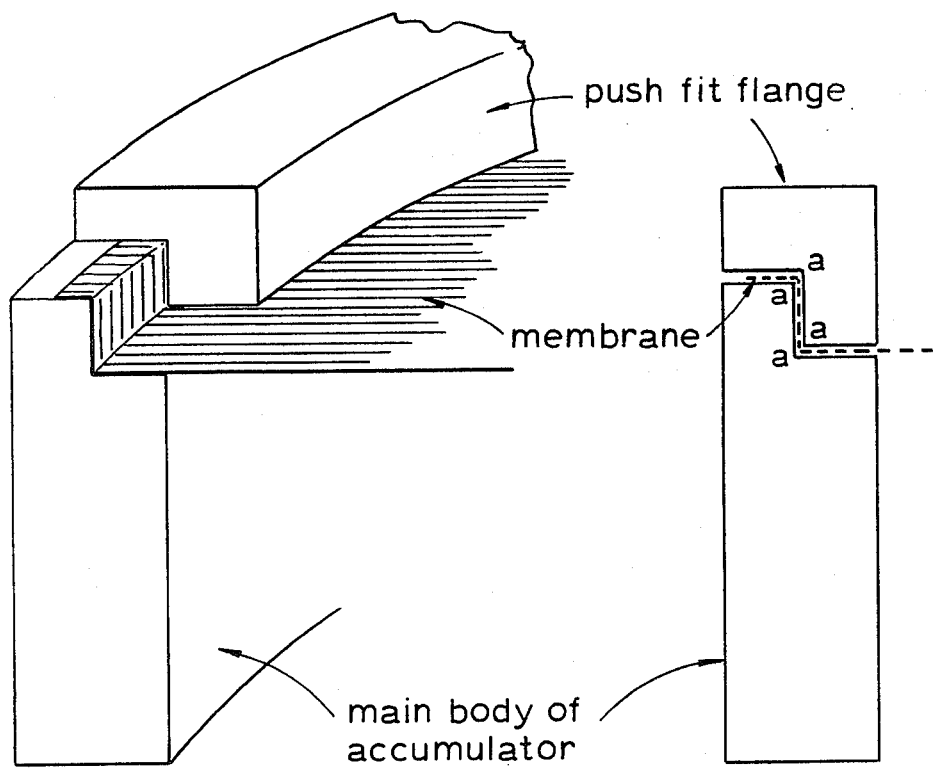

A simple push-fit flange (as shown in FIG. 16 of the accompanying drawings) was devised to overcome this problem.

However great care had to be taken not to split the membrane by overstretching it at the right angle corners (marked 'a' in FIG. 16) during the push-fit operation. This problem was minimised, but not completely overcome, by rounding off the corners. By precision engineering and careful fitting, it was possible to achieve excellent membrane seals.

One unexpected problem that has been observed with the plastic accumulators (not observed with glass accumulators) was the appearance of an air bubble between

7. EXPERIMENTAL

Accumulator

All experiments were done in an accumulator according to FIG. 1 of the drawings using cellophane membranes. The majority of experiments were done with accumulators containing dithizone as trapping agent dissolved in carbon tetrachloride. The concentration of dithizone in carbon tetrachloride was 100 mg $l^{-1}$ in all such experiments. Several experiments were also effected using dibenzoyl methane as a trapping agent dissolved in carbon tetrachloride.

Bicarbonate solution of Copper and Zinc

Sodium bicarbonate solutions ($10^{-3}$M to 5 × $10^{-3}$M) were prepared by diluting stock solutions of A.R. grade sodium bicarbonate. Stock copper solution (1 $gl^{-1}$ $Cu^{2+}$) was prepared by dissolving A.R. grade $CuSO_4.5H_2O$ in distilled water. Dilute solutions of copper were prepared by diluting aliquots of the stock copper solution with bicarbonate solution. The pH values of the bicarbonate solutions were previously reduced to less than 6 by passing carbon dioxide to avoid premature formation of non-equilibrium species. The pH value of each copper bicarbonate solution was then raised to the desired value by passing air (or nitrogen) to remove carbon dioxide. It has been shown (Stiff, Water Research, 5, 1971, 171–176) that the addition and removal of carbon dioxide to adjust pH does not detectably affect the bicarbonate concentrations and does not, of course, alter the solution's ionic strength. Each solution was stood at ambient temperature for between 0.5 and 1hour before commencing the accumulation experiment.

Stock solutions of zinc (1 $gl^{-1}$ $Zn^{2+}$) were prepared by dissolving zinc metal in concentrated nitric acid and evaporating off excess acid. Dilutions were made with sodium bicarbonate using the procedure described for copper. Some experimets were done in which tap water was used to make up stock solutions of copper or zinc.

Glycine solutions of copper and zinc.

Solutions of A.R. glycine in distilled water, or in some cases tap water, were used to dilute stock solutions of copper and zinc. Since the concentrations of copper and zinc were higher than those likely to be found in natural waters, the concentration of aminoacid was increased accordingly. High pH (7) solutions were achieved by using tap water.

Humic Acid — Copper Complex

Humic acid solution was made according to the method of Gardiner (Water Pollution Research Centre report No. 1273, July 1973). 2.0 g commercial humic acid (Aldrich Chemical Co.) was extracted with 9.0 g sodium bicarbonate in 300 ml water with intermittent stirring for 1hour. The brown solution was filtered free of undissolved solid and treated with 50% A.R. hydrochloric acid until excess bicarbonate had reacted and the pH value was about 1. At this stage, the solution became slightly cloudy. This mixture was extracted with 200 ml followed by 100 ml n - hexanol, leaving a very pale yellow aqueous layer. The organic layer was evaporated to dryness using an infra-red lamp.

A solution of arbitrary concentration was made by adding 66.0 mg extract to about 25 ml water containing 3 ml of 0.1 M sodium hydroxide (since the solid dissolved with difficulty in neutral water). The pH of the solution was adjusted to about 10.5 by the addition of 0.1 M hydrochloric acid and diluted to 100 ml.

A dilute solution containing 86 mg $l^{-1}$ humic acid and 3 mg $l^{-1}$ $Cu^{2+}$ was prepared from the above solution and from a stock solution of $Cu^{2+}$ in distilled water using $10^{-3}$ M sodium bicarbonate solution as diluent. The final pH of this solution was 8.02. This solution was used for accumulation experiments.

It was assumed that all copper was complexed by the humic acid and that the addition of dilute sodium bicarbonate did not reduce the extent of copper-humic acid complexing.

Calculation of ratio of metal-ion complex to free metal ion

Using reported stability constant data (Stiff, Water Research. 5, 1971, 171 – 176; Sillen and Martell, Special Publication No. 17, Chemical Society (1964)) the approximate ratios of metal-ion complex to free metal ion at the start of the accumulation experiment were calculated from the following equations:

| 1. Copper-bicarbonate system | |
|---|---|
| $[HCO_3^-] [CO_3^{2-}] [H^+]$ | $= 10^{10.3}$ |
| $[CuCO_3] / [CO_3^{2-}] [Cu^{2+}]$ | $= 10^{6.8}$ |
| $[CuCO_3] / [Cu^{2+}]$ | $= [HCO_3^-] / [H^+] \times 10^{3.5}$ |

| 2. Zinc-bicarbonate system | |
|---|---|
| $[HCO_3^-] / [CO_3^{2-}] [H^+]$ | $= 10^{10.3}$ |
| $[ZnCO_3] / [CO_3^{2-}] [Zn^{2+}]$ | $= 10^{5.2}$ |
| $[ZnCO_3] / [Zn^{2+}]$ | $= [HCO_3^-] / [H^+] \times 10^{5.1}$ |

| 3. Copper-glycine system | |
|---|---|
| $[LH] / [L^-] [H^+]$ | $= 10^{9.9}$ |
| $[CuL^+] / [L^-] [Cu^{2+}]$ | $= 10^{8.6}$ |
| $[CuL^+] / [Cu^{2+}]$ | $= [LH] / [H^+] \times 10^{1.3}$ | where
HL = glycine

| 4. Zinc-glycine system | |
|---|---|
| $[LH] / [L^-] [H^+]$ | $= 10^{9.9}$ |
| $[ZnL^+] / [L^-] [Zn^{2+}]$ | $= 10^{5.5}$ |
| $[ZnL^+] / [Zn^{2+}]$ | $= [LH] / [H^+] \times 10.44$ |

8. Summary and Conclusions

1. The study of the accumulation by dithizone in carbon tetrachloride of copper and zinc in those forms likely to be present in natural waters, viz. the free metal ion ($M^{2+}$), the carbonate complex ($MCO_3$) and the 1:1 metal : amino acid complex ($ML^+$), (using glycine as a model) showed that significant accumulation of copper from $Cu^{2+}$ — $CuCO_3$ ($P_{aq}$ 8-17 × $10^{-4}$ cm.sec$^{-1}$) systems occurs below pH 7, even when the ratio of complex to free metal ion is high. The rate of accumulation was reduced when the pH exceeded 7 and the ratio of complex to free metal ion was further increased.

The effect of pH (5.5-8.1) on accumulation of zinc from $Zn^{2+}$ — $ZnCO_3$ ($P_{aq}$ = 6-11 × $10^{-4}$ cm. sec$^{-1}$) and $Zn^{2+}$ — $ZnL^+$ ($P_{aq}$ = 6-17 × $10^{-4}$ cm.sec$^{-1}$) was much less than in the case of copper.

The rate of accumulation of metal ions by the accumulator was determined from equation (iv) above, namely:

$$\frac{dM}{dt} = P.A.C. \qquad (iv)$$

where
$M$ = mass of metal accumulated in time $t$
$P$ = permeability constant of the membrane
$A$ = cross-sectional area of the membrane
$C$ = average concentration of metal passing over the membrane in time $t$.

Our laboratory experiments showed that values of P of between $10^{-4}$ and $10^{-3}$ cm. sec$^{-1}$ are obtained for accumulation from aqueous systems of mercury ($Hg^{2+}$), copper ($Cu^{2+}$, copper carbonate complex, copper amino acid complexes) and zinc ($Zn^{2+}$, zinc carbonate complex, zinc aminoacid complexes) compounds.

The data showed that the accumulator could be used to monitor copper and zinc in the field.

2. The investigation indicated that copper is not accumulated by dithizone in carbon tetrachloride from a copper - humic acid complex (pH 8).

3. An IRI simulated river system was designed.

The field trials extending over a six month period are now discussed.

(I) EXPERIMENTAL (A) Accumulator Design (i) Plastic accumulators. Preliminary laboratory work was done exclusively with glass accumulators. It was thought that glass devices might be unsuitable for field use due to the ease with which they might be broken. This was subsequently shown not to be a problem. The possibility of using plastic accumulators was therefore suggested. However, design studies (vide infra) showed that plastic accumulators were, in fact, less suitable due to a variable tendency to leak and the possible presence of metals in the plastics material which were extracted by the trapping agent (practically all commercial polymers contain metal ions, albeit in very low concentrations, and although they may be slowly removed from the plastics material by aqueous systems, they are more likely to interact with complexing agents and therefore to produce a variable source of contamination).

Figure 17:
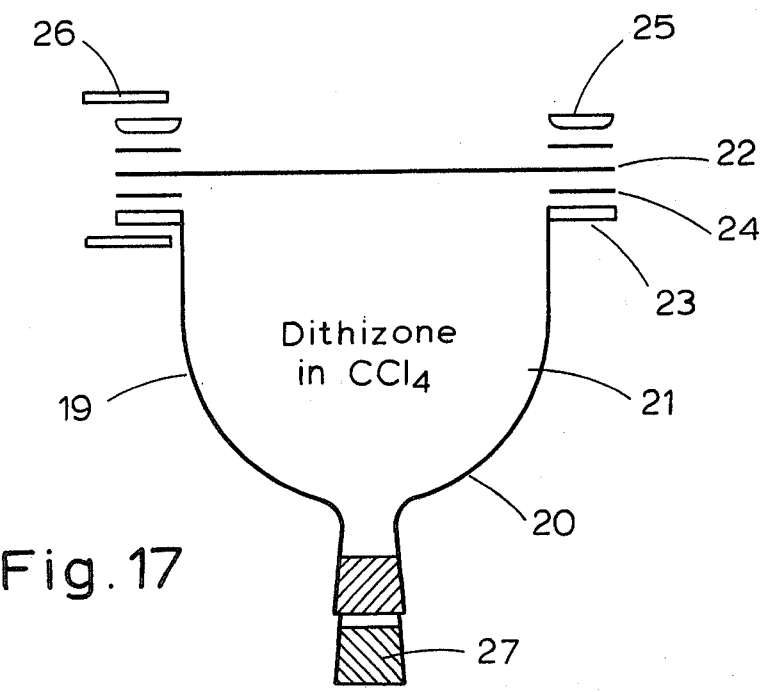

(ii) Glass accumulators and method of fixing accumulators in river. The design of glass accumulators adopted for field work was that shown in FIGS. 17 and 18 of the accompanying drawings. FIG. 17 is an axial section of the accumulator; and FIG. 18 is a sectional elevation of the device of FIG. 17 in position on a river bed.

The device 19 shown in FIG. 17 comprises a glass container 20 filled with a solution 21 of dithizone in carbon tetrachloride. The glass container 20 is covered with a membrane 22 which is held in place by means of a ground glass flange 23, two gaskets 24 and a holding ring 25 having chamfered edges which prevent the membrane from splitting. The flange 23, the gaskets 24, the holding ring 25 and the membrane 22 are fixed in position by means of a flange clamp 26. The glass container 20 is provided with an opening 27 for filling and emptying purposes.

Figure 18:
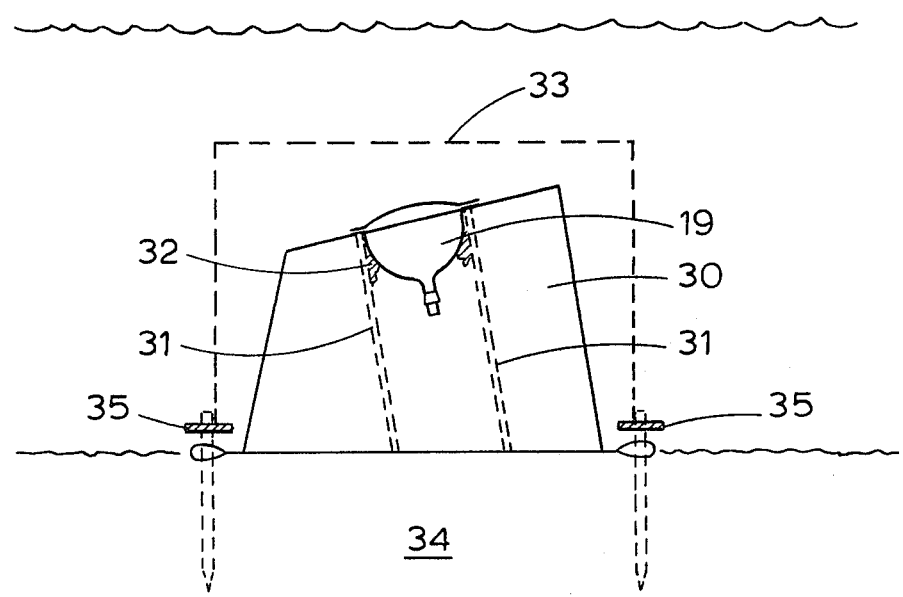

FIG. 18 shows the device 19 fitted into a concrete block 30 with the aid of pipes 31 set into the concrete block 30. The device 19 is supported in position by means of foam supports 32. The device 19 and concrete block 30 are covered by a plastics coated wire cage 33 which is held in position on a river bed 34 by means of stakes 35.

The holding ring was 4 mm thick, the polythene gasket was 0.5 mm thick and the membrane area was about 44 cm$^2$. The volume when full with trapping agent was about 400 to 700 ml.

Experiments showed that, while the concrete blocks remained stationary in slow to medium flowing water, in heavy spate conditions they were sometimes shifted a few yards downstream. To overcome this problem, the accumulators were staked into the river bed using the procedure shown in FIG. 18.

The plastics coated wire cages prevented large stones from damaging the membranes. They were particularly useful in collecting leaves and weed, which otherwise could block the membrane surface.

B. Accumulator Preparation: Installation in and Removal from River.

(i) Filling procedures. The trapping agent solution, (100 ml/l dithizone in carbon tetrachloride; 5 or 10l) was prepared 24h before use. It was stored in a 10l stoppered flask and dispensed into the accumulators from a separating funnel. Membranes were cut approximately to size and soaked in distilled, deionised water overnight to remove plasticiser. Polythene gaskets were treated similarly.

The accumulators were assembled as follows (see FIG. 17):

(a) support accumulator in cork ring,
(b) locate polythene gasket,
(c) locate membrane ensuring uniform tension,
(d) locate second polythene gasket,
(e) locate thick plastic fixing ring (~4 mm thick),
(f) fasten clamp,
(g) invert accumulator and fill with trapping agent solution (excessive membrane expression is prevented by means of a back plate placed against the membrane during filling).

The whole operation was done as quickly as possible (~1-2 min) to minimize the time that the membrane surface was exposed to the atmosphere.

(ii) Location in river. The accumulator was then placed, membrane upwards, in a plastic bucket of distilled water and transported to the river bank. The accumulators were removed from the buckets and located in the concrete blocks. The space between the accumulator and the concrete wall was packed with ½ inch thick polyurethane foam to provide a firm fit. The plastics coated wire cages were then placed over the concrete blocks and secured with wire ties. The complete assembly was then placed at the chosen site in the river.

The site (in the R.Esk near to the Musselburgh gauging station) was chosen so that the entire assembly was about 6 inches below the surface of the water when the river was at its normal lowest level, and the river bed was sufficiently soft to accept holding stakes for the accumulators. The accumulators were placed close to one another giving mutual support by shared stakes, with the membranes inclined at about 20° to the flow of water. It was hoped that this 'close packing' would minimize differences in physical conditions between accumulators.

The accumulators were inspected regularly (usually once a day) during the trial period.

(iii) Removal from river. At the end of a trial, the assembly was removed to the river bank, and any twigs, leaves or other debris were detached from the cage. The cage was removed from the block and the accumulator and membrane rinsed rapidly with distilled, deionised water to remove any dirt or small particles. The accumulator was then placed horizontally (membrane face up) in a bucket filled with distilled, deionised water and returned to the laboratory.

At the laboratory, the external surface of the accumulator was rinsed again with distilled, deionised water and the contents were emptied into a 0.5l measuring cylinder.

The volumes of the organic phase and any aqueous phase were measured. Any small amounts of water were removed by pipette. The accumulator was washed twice with fresh carbon tetrachloride which was added to the measuring cylinder. The entire contents of the measuring cylinder were emptied into a rotavapour flask and evaporated to dryness at ~60° C under vacuum. This sample was then prepared for chemical analysis (vide infra).

C. Constant Flow Tank in Gauging Station

Figure 19:
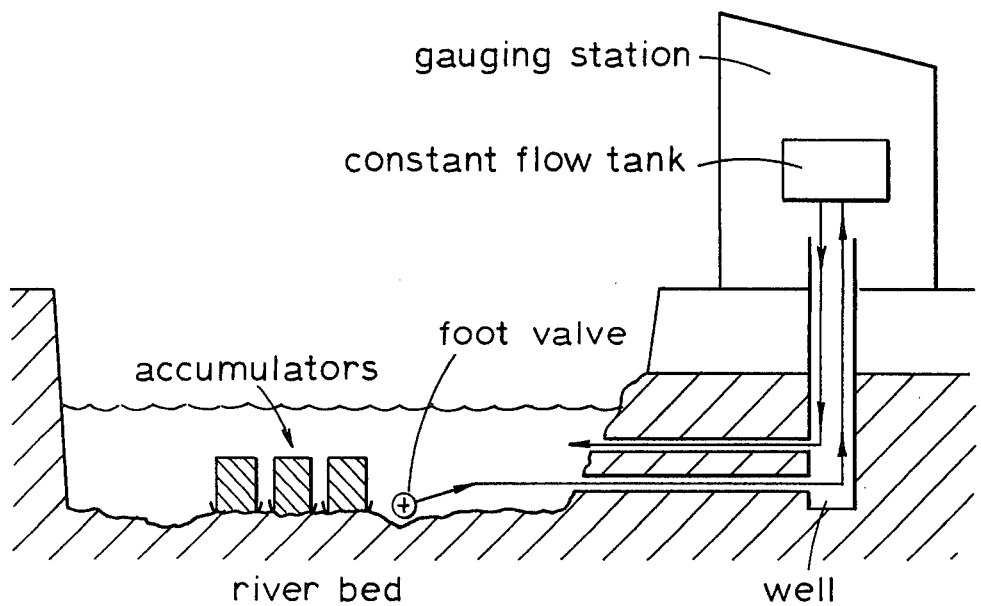
Figure 19:
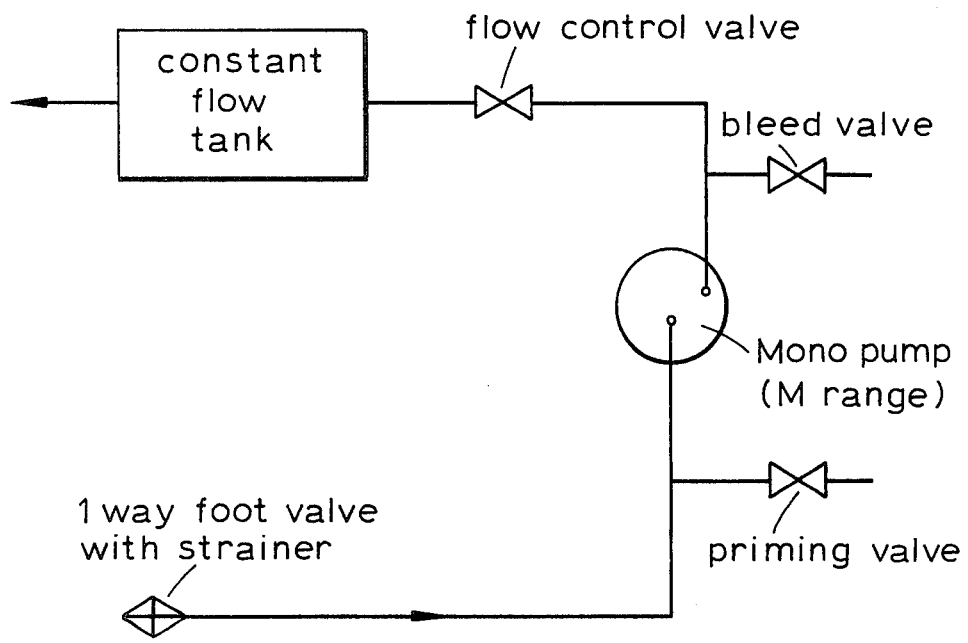
Figure 21:
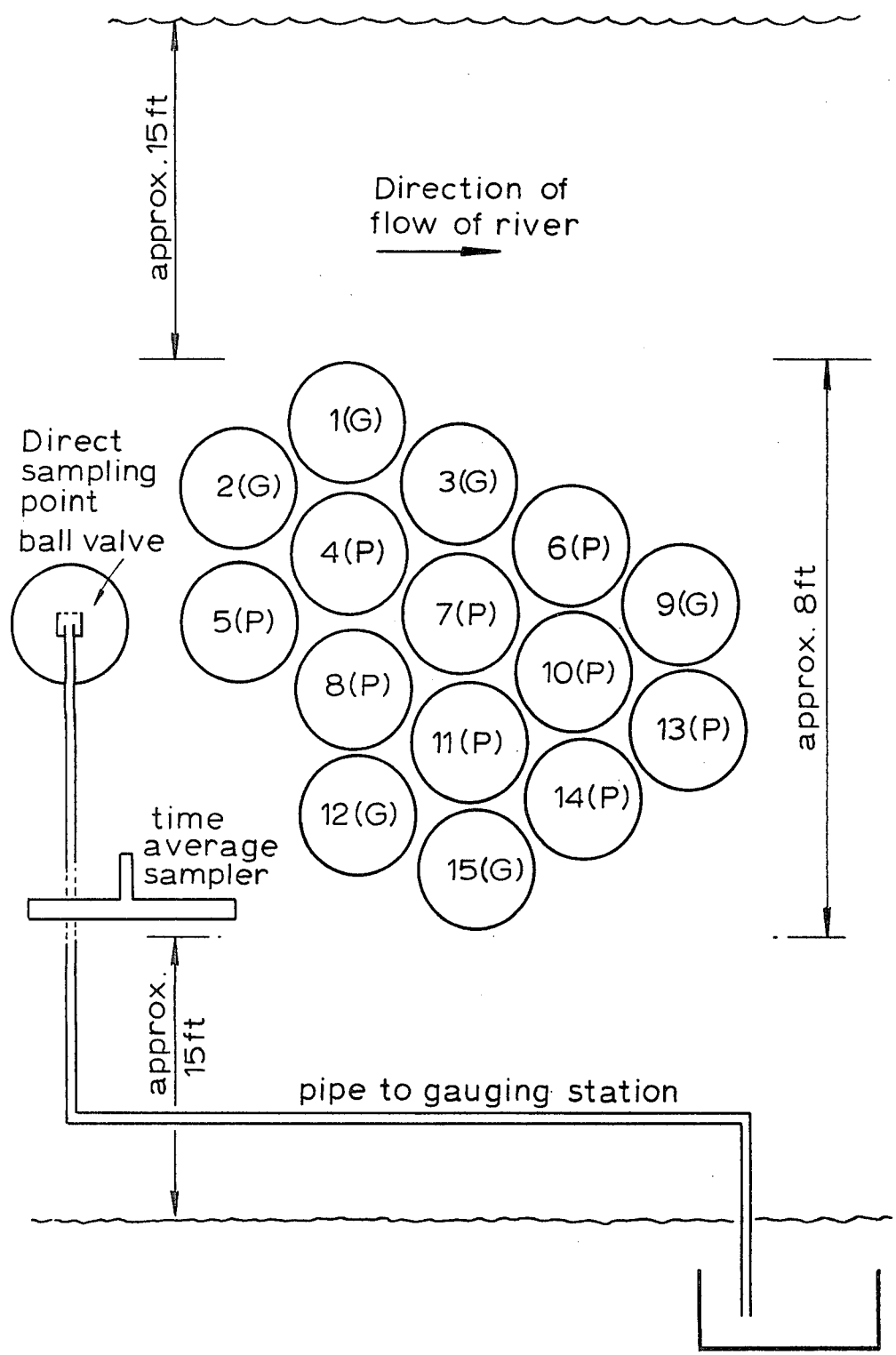

In addition to experiments in the river, a limited number of accumulation experiments were conducted in a tank installed in a gauging station which was adjacent to the main river site of the trials. The construction of this system is shown diagrammatically in FIG. 19. Water is drawn from a point in the river close to the accumulator site and pumped to the gauging station (~15 ft head), through the constant flow tank at an arbitrary rate of 10l/min, and returned to the river.

Figure 20:
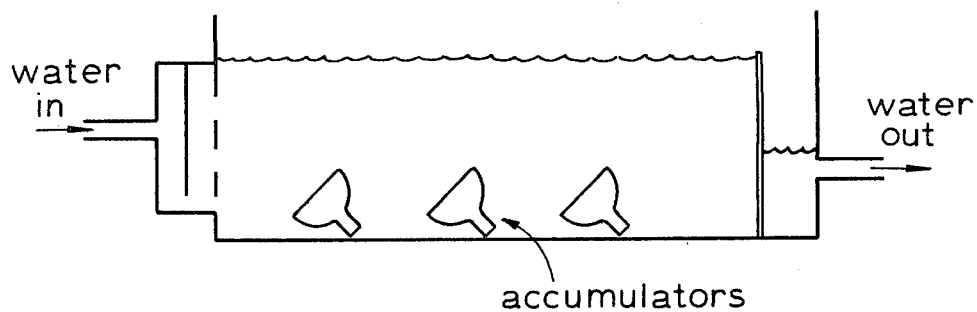
Figure 20:
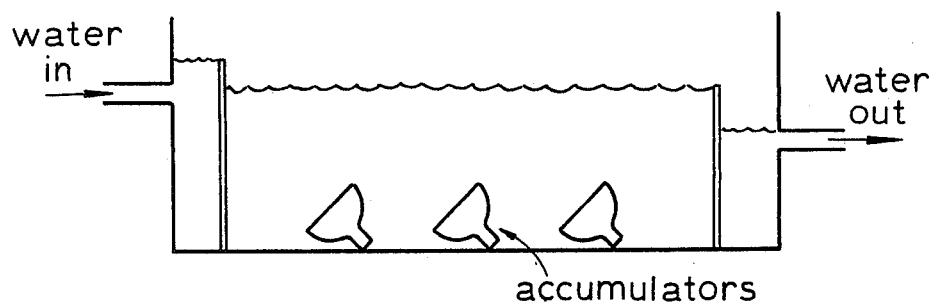

Two designs of constant flow tank were investigated. The initial design (FIG. 20) suffered from the fault that, when the water flow stopped because of blocking of the foot-valve by leaves, the level of water in the tank dropped to below that of the accumulators, thus exposing the membranes to the atmosphere. This problem was eliminated by changing the position of the inlet and outlet pipes (FIG. 20). Blocking of the foot-valve by leaves and weeds was minimised by enclosing the foot-valve within a small ¼ inch mesh cage.

D. Procedures for Sampling River Water.

All containers and sampling equipment were steeped in 10% nitric acid and rinsed in distilled, deionised water before use. Three methods were used for sampling the river water:

(a) Direct samples during field trials. Five samples were taken daily at two hourly intervals between 0900 and 1700 h direct from the river about one yard upstream from the accumulators. Only one sample was taken on Saturdays and Sundays.

(b) Time average samples. Approximately 11 samples were collected over 24h periods using the time average sampler (Quantum Science 1500 liquid sampler) submerged alongside the accumulators.

(c) Time average samples. Approximately 750 ml samples were collected over 24h using a Watson Marlow peristaltic pump to draw water from the inlet of the constant flow tank located in the gauging station.

These aqueous samples were collected in 1l polythene bottles, and were filtered as soon as possible in the laboratory (Amicon Stirrer Cell Model 402 operating under a nitrogen pressure of about 10 p.s.i.; Whatman GF/A filter placed on top of an Amicon 0.45 μm Diaflo ultrafiltration membrane; both filters previously washed with 10% nitric acid and distilled, deionised water until neutral). The first 50 ml of each filtrate were discarded and the following 100 ml were collected in small polythene bottles and acidified with 1 ml conc. nitric acid. Between samples, the filters were washed with distilled water and replaced after the filtrationn of 4 samples when the rate became excessively slow. The pH of the filtered samples was measured before acidification. These solutions were analysed by atomic absorption spectrophotometry.

E. Analytical Procedures

Standard analytical procedures were used.

Metal analysis was done by atomic absorption spectro-photometry using a Varian 1200 spectrophotometer equipped for both flame and carbon rod atomisation.

(II) RESULTS

A. General Observations

Accumulator design and construction

As indicated above, glass accumulators were preferred to plastic accumulators for the reasons given. All field work was done at a site in the R.Esk adjacent to the Musselburgh gauging station. The shallowness of the central part of the river (normally knee deep in the absence of heavy rain) allowed easy access. The method of locating the accumulators in the river was satisfactory for shallow sites (no more than mid-thigh deep), but modifications to the locating system might have to be made for deeper or less accessible sites.

Accumulator assembly — mechanical stability in river

The assembly of the accumulators was a straight-forward operation but care and some practice were needed before repeated assemblies could be made without breaking the membrane (the membrane is the weakest mechanical part of the device during assembly but once the device is filled with trapping agent solution, the membrane will stand up to considerable pressure and knocks). It is important to ensure that the membrane is uniformly tensioned over the flange joint and that the 4mm thick holding ring (FIG. 17) has bevelled edges which will not cut the membrane when the joint is clamped. With few exception, the membranes exhibited good mechanical stability in the field. Membrane splitting occurred more frequently in the early stages of the trials and was invariably due to incorrect tensioning rather than damage by moving objects in the river. The 1 inch mesh protective cages were effective in preventing large stones from impinging on the membrane during heavy spate conditions. The cages were also extremely effective in trapping leaves and weed, but still allowed normal water flow across the membranes.

The initial field work was started at a time when trees along the river bank were shedding their leaves and during this time it was necessary to remove trapped leaves from the cages every day. When this seasonal event was past, the cages remained relatively free from trapped debris.

It was not necessary to stake the assemblies into the river bed when the river was in normal flow. However, the first spate resulted in the loss of some assemblies which were swept downstream and could not be found. Thereafter, the assemblies were firmly staked to the river bed.

Biochemical stability. It was observed that membranes (regenerated cellulose) showed distinct evidence of biodegradation when they were immersed alone in the river for between 3 and 6 weeks. However, none of the accumulator membranes showed evidence of biodegradation after eight weeks' immersion in the river. This biochemical stability is probably due to the antibacterial action of carbon tetrachloride which occurs at the water-solvent interface in the membrane.

Water in accumulators. With few exeptions (see Table 11 below), variable amounts of water were found in accumulators when they were removed from the river. This effect was never observed in laboratory experiments with glass accumulators. Initially, it was thought that the effect was a result of inefficient sealing at the membrane-gasket interface; this was certainly the case with the plastics accumulators.

TABLE 11

| | | | Conditions of Accumulators after Trials | | | |
|---|---|---|---|---|---|---|
| Accumulator No. | Material plastic (P) or glass (G) | Time in river, days | Volume liquid on removal from river (ml) | | Condition of membrane and other observations. | |
| | | | $CCl_4$ | $H_2O$ | | |
| FIELD TRIAL II — accumulators inclined upstream and downstream | | | | | | |
| 1 | P | 10 | 465 | 30 | good | (upstream) |
| 2 | P | 10 | 490 | 30 | good | (downstream) |
| 3 | G | 10 | 265 | 95 | broken | (upstream) |
| 4 | G | 10 | 360 | 10 | good | (downstream) |
| FIELD TRIAL III — accumulators inclined downstream | | | | | | |

TABLE 11-continued

Conditions of Accumulators after Trials

| Accumulator No. | Material plastic (P) or glass (G) | Time in river, days | Volume liquid on removal from river (ml) CCl₄ | Volume liquid on removal from river (ml) H₂O | Condition of membrane and other observations. |
|---|---|---|---|---|---|
| 1 | G | 7 | 385 | 15 | |
| 2 | G | 7 | 385 | 10 | |
| 3 | G | 7 | 380 | 5 | All membranes in glass |
| 9 | G | 7 | 370 | 10 | accumulators were in good |
| 12 | G | 7 | 380 | 0 | condition. |
| 15 | G | 7 | 380 | 0 | |
| T1 | G | 7 | 330 | 10 | |
| T2 | G | 7 | 390 | 0 | |
| T3 | G | 7 | 440 | 0 | |
| 4 | P | 7 | 440 | 40 | |
| 5 | P | 7 | 430 | 50 | |
| 6 | P | 7 | 455 | 30 | Membranes on some plastic |
| 7 | P | 7 | 490 | 30 | accumulators had sagged. |
| 8 | P | 7 | 440 | 35 | |
| 10 | P | 7 | 345 | 35 | |
| 11 | P | 7 | 390 | 35 | |
| 13 | P | 7 | 460 | 10 | |
| 14 | P | 7 | 510 | 30 | |
| T4 | P | 7 | 520 | 10 | |
| FIELD TRIAL IV — accumulators inclined upstream | | | | | |
| 1a | G | 7 | 390 | 2 | good |
| 1b | G | 7 | 390 | 10 | good |
| 2a | G | 14 | 380 | 10 | slight split in membrane |
| 2b | G | 14 | 365 | 10 | membrane broken on removal |
| 2c | G | 7 | 350 | 40 | membrane broken on removal |
| 2d | G | 7 | 390 | 5 | good |
| 3a | G | 21 | 380 | 10 | good |
| 3b | G | 21 | — | | broken |
| 3c | G | 7 | 370 | 5 | good |
| 3d | G | 7 | 390 | 5 | good |
| 4a | G | 28 | 390 | 10 | good |
| 4b | G | 28 | 350 | 15 | good |
| 4c | G | 28 | 330 | 30 | good |
| FIELD TRIAL V — accumulators inclined upstream | | | | | |
| R1 | G | 8 | 325 | 15 | good |
| R2 | G | 8 | 360 | 10 | good |
| R3 | G | 8 | 360 | 10 | good |
| R4 | G | 8 | 350 | 10 | good |
| R5 | G | 8 | 360 | 10 | good |
| R6 | G | 8 | 325 | 20 | good |
| R7 | G | 8 | 350 | 15 | good |

Footnote:
(a) The variable volume of CCl₄ is due to variations in the internal volumes of the accumulators and to variable bowing of the membrane when the accumulator is full.
(b) Membrane areas were approx. 44 cm² (glass accumulator) and 70 cm² (plastic accumulator).
(c) Accmulators with no code T refer to experiments in the constant flow tank in the gauging station.

However, water present in the swollen membrane when the accumulator is assembled may subsequently assist the further transfer of river water across the membrane until the water-carbon tetrachloride interface is at, or near, equilibrium. Experiments in the constant flow tank, where regular observations are easily made, established that water transfer occurred during the first two or three days' immersion and thereafter there was little further transfer.

The presence of such small amounts of water (Table 11, glass accumulators) is unlikely adversely to affect the operation of the accumulators which are inclined at about 20° to the horizontal, so that the water, being less dense than the trapping agent solution, settles at the top of the device and does not effectively reduce the water-solvent interfacial area.

Subsequently, with better experience in membrane fitting, it was observed that water was rarely present in the accumulator even after several weeks' immersion.

B. Analytical Data and Interpretation of Field Trials.

The first three months of the six-month project were devoted to design and manufacture of accumulators and investigation of methods for fixing them in the river. The last three months were devoted to accumulator trials in the river and chemical analysis of accumulators and river water. At this time and under poor weather conditions, it was necessary to conduct consecutive accumulation trials without the hindsight of analytical data which were obtained in full towards the end of the project.

The amounts of metals present in the R.Esk are relatively low (e.g. Table 13 below; approximate average conditions 0.005 $\mu$g/ml copper, 0.001$\mu$g/ml lead, 0.001 $\mu$g/ml cadmium and 0.03 $\mu$g/ml zinc). The theoretical rates of accumulation of these metals from the river by an accumulator are given by equation (iv) above $$dM/dt = PAC \qquad (iv)$$

where:
$M$ = mass metal accumulated in time $t$;
$P$ = membrane permeability constant;
$A$ = membrane area; and
$C$ = average metal concentration in river during time $t$.

The rates of accumulation from the river are likely to be less than those found in earlier laboratory experiments since (a) river temperatures were some 10° – 15° C lower than laboratory temperatures (diffusion in membranes is temperature-dependent);

(b) there is considerably less agitation at the membrane surface in the river than in the laboratory system; and (c) some of the metals present in the river are likely to be present in strongly complexed forms which will not react with the trapping agent.

Assuming a value for P of $10^{-4}$ cm sec$^{-1}$ and using the river metal concentrations quoted above, the theoretical rates of accumulation by devices with 44 sq.cm. areas were calculated as follows:

(d) 13.8 μg copper per week;

(e) 2.76 μg cadmium per week; and (f) 82.2 μg zinc per week.

The amounts of metal found in the trapping agent solution (after processing and concentrating for analysis) were of the same order of magnitude as these theoretical values.

The actual results were as follows:

Field Trail I

First accumulator performance trial. 14-10-74 to 21-10-74

Two plastics accumulators were placed in the centre of the river, membranes inclined downstream, and left undisturbed for one week. Daily inspection was made, without touching the accumulators, to ensure that their position was not affected by river flow, which was relatively slow during this period. At the end of one week, the membrane was found to be in a good condition. Used membranes were usually stained reddish purple.

Field Trial II

Second accumulator performance trial. 24-10-74 to 4-11-74

This trial was designed to test whether there were likely to be any differences in the mechanical stability of plastics and glass accumulators inclined towards and away from the direction of river flow. It also afforded the first opportunity to test proposed sample preparation techniques and establish likely analytical working ranges.

Two plastics and two glass accumulators were placed in the centre of the river with one of each type inclined upstream and downstream. After 10 days, the accumulators were removed. Three were in good condition but the membrane of one of the glass accumulators which had been inclined upstream was split; it was not known whether the split was caused by river debris impinging on the membrane or whether the clamp had been excessively tightened during the filling operation.

Experiments were conducted with the carbon tetrachloridedithizone solutions taken from the accumulators in an attempt to optimise sample preparation procedures and analytical working ranges (see Experimental).

Field trials I and II showed, with one exception, that the design adopted withstood the physical conditions in the river. The concrete blocks appeared to protect the glass accumulators adequately.

Field Trial III

Experiment to investigate reproducibility of metal accumulation. 31-10-74 to 6-11-74

Six glasses and nine plastic accumulators were placed in the centre of the river in the configuration shown in FIG. 8, all with membranes inclined downstream. This configuration was adopted to minimize any across-river variations in metal content. In addition three glass and one plastic accumulators were placed in the constant flow tank in the gauging station for the same period of time as those in the river.

During the trial the river water was sampled as follows: five direct daily samples, one 24h time average sample from a point in the river close to the accumulators, and one 24h time-average sample from the inlet of the constant flow tank.

After 7 days the accumulators were removed from the river and examined. Glass accumulators were processed and analysed. All river water samples were also analysed. Results are summarised as follows:

(i) All plastic accumulators and half of the glass accumulators contained water. The amount of water present in glass accumulators (5 – 10 ml) was considerably less than that in plastic accumulators (10 – 50 ml) (Table 11).

(ii) None of the glass accumulators were broken.

(iii) All the membranes in the glass accumulators were intact and in good condition. Some membranes in the plastic accumulators had noticeably sagged, especially those in accumulators containing the larger quantities of water.

(iv) The analytical results on the glass accumulators are shown in Table 12. These results refer to metal found in the trapping agent solution only. (Earlier laboratory work on the accumulation from systems with high metal concentrations (~5 mg/l) established that the amount of metal retained in the membrane was very small compared to that found in the carbon tetrachloride-dithizone. It was assumed, erroneously as it turned out, that a similar effect would be found in accumulators operating in rivers with low metal concentrations; for this reason membranes were not analysed at this stage).

TABLE 12

Field Trial III. Metal (μg) accumulated in carbon tetrachloride-dithizone solution in glass accumulators (membranes not analysed) over the 7 day period 31-10-74 to 6-11-74.

| Accumulator No. | Total metal found, μg | | | |
|---|---|---|---|---|
| | Cu | Pb | Cd | Zn |
| Experiment directly in river | | | | |
| 1 | 10. | 1 | 0.4 | 12 |
| 2 | 3.5 | 1 | 0.3 | 8 |
| 3 | 4.5 | 2 | 0.3 | 9 |
| 9 | 5.5 | 3 | 0.4 | 6 |
| 12 | 3.5 | 2 | 0.3 | 6 |
| 15 | 3.0 | 0.5 | 0.8 | 10 |
| Experiments in tank in gauging station | | | | |
| T1 | 5.0 | 1 | 0.5 | 7 |
| T2 | 3.0 | 1 | 0.5 | 5 |
| T3 | 1.5 | 1 | 0.1 | 4 |

(a) Results are given to appropriate significant figures, bearing in mind concentration steps used and sensitivities, as stated in Table 1.
(b) See footnote (c), Table 7.

The results in Table 12 show that in the glass accumulators, metals were present in decreasing order of Zn > Cu > Pb ≧ Cd; this order is similar to that found in river water per se (Table 4). (Polypropylene devices are considered unsuitable for metal accumulation because of the relatively high levels of metals present in the plastic which can react with the trapping agent).

Results for accumulators located in the gauging station were similar to those for accumulators in the river.

Analysis of the river water (Table 13) showed that the levels of all four metals were very low and there was no evidence of 'peaking'. Correlation between the three sampling methods was good.

Field Trial IV

Extended accumulation experiment. 20-11-74 to 20-12-74

The objective of this experiment was to attempt to relate the amounts of metal accumulated to the times of accumulation over a six week period.

Twelve glass accumulators, membranes inclined upstream were placed in the middle of the river. The plan was to remove two accumulators at the end of each week and replace them by a further two accumulators which would themselves remain in the river for one week only, thus relating the total metal accumulated after, say, $n$ weeks to that accumulated after $(n + 1)$ weeks.

TABLE 13

Analysis of river water during Field Trial III

| Day | Sample procedure | pH | Cu | Pb | Cd | Zn |
|---|---|---|---|---|---|---|
| 1 | S | 8.0 | 0.005 | nd | 0.0005 | 0.04 |
| 1 | P | 7.8 | 0.005 | 0.005 | 0.0005 | 0.04 |
|   | D | 7.8 | 0.005 | nd | 0.0005 | 0.03 |
|   | S | 7.8 | — | — | — | — |
| 2 | P | 8.1 | 0.005 | nd | 0.001 | 0.07 |
|   | D | 7.7 | 0.003 | nd | 0.001 | 0.02 |
|   | S | 7.9 | 0.003 | nd | 0.0005 | 0.02 |
| 3 | P | 8.0 | 0.005 | nd | nd | 0.02 |
|   | D | 7.9 | nd | nd | 0.001 | 0.02 |
|   | S | 7.9 | 0.005 | nd | 0.001 | 0.05 |
| 4 | P | 8.0 | 0.005 | nd | 0.002 | 0.55 |
|   | D | 8.0 | 0.005 | nd | 0.001 | 0.20 |
|   | S | 7.9 | 0.005 | nd | 0.0005 | 0.03 |
| 5 | P | 8.0 | 0.005 | nd | 0.0005 | 0.04 |
|   | D | 7.9 | 0.015 | nd | 0.001 | 0.06 |
|   | S | 8.1 | 0.02 | nd | 0.0005 | 0.06 |
| 6 | P | 8.2 | 0.01 | nd | nd | 0.06 |
|   | D | 7.9 | 0.01 | 0.005 | 0.001 | 0.10 |

Code:
S = time average samples taken over 24h period in time average sampler located in river.
P = time average samples taken over 24 h by peristaltic pump operating in gauging station.
D = average of (usually) 5 direct samples taken at approx. 2 hourly intervals over the working day; little variation between samples.
nd = not detected, Limit of detection is 0.005 µg/ml for lead.

During the trial, river water was sampled by the three methods described previously.

The trial ran without incident for three weeks. During this time, rainfall increased and it became difficult to conduct manual operations in the river. During the fourth week, the river level rose considerably (the highest for three years) and much debris (ranging from wood and stones and metal articles including an old bicycle frame) were swept over and/or close to the accumulator site. Inspection of the site was made as soon as the river dropped to a reasonable level. Some of the concrete blocks had been shifted from their original position and the membranes of four accumulators were broken. It was decided to terminate the trial, at this stage.

A similar experiment, using half the number of accumulators used in the river, was started in the constant flow tank at the start of the river trial. This experiment was abandoned after two weeks because reasonably constant flow conditions could not be achieved: the foot-valve (FIG. 19), became repeatedly blocked up with weed, despite the application of several different mesh cages around it.

The results obtained are given in Tables 14 to 16 below.

The river Esk was chosen for initial field trials because of its proximity to the laboratory rather than for its high or variable metal content. In fact, the river was essentially unpolluted by industrial effluent and the metal content was relatively low. Because of this, it was not possible to obtain good correlation of metal accumulation with metal content of river water in the initial trials, as explained below.

Metals were present in the trapping agent solution in decreasing order Zn>Cu>Pb>Cd. There was no evidence of steady accummulation of copper and lead over the four weeks' period; however, steady accummulation of small quantities of these metals could be missed in the presence of high 'blank' and/or 'control' levels. Longer accummulation times in a more "polluted" river would have given more positive information.

TABLE 14

Field Trial IV. Metal (µg) accumulated in carbon tetrachloride-dithizone solutions (excluding metal in membranes) over the 4 week period.

| Accumulator No. | Time in river, days | Metal present in $CCl_4$ - dithizone soln., µg | | | |
|---|---|---|---|---|---|
| | | Cu | Pb | Cd | Zn |
| 1a | 7 | 4.9 | 1.9 | 2.2 | — |
| 1b | 7 | 4.5 | 2.5 | 0.45 | 60 |
| 2c | 7 | 4.9 | 2.5 | 0.3 | 25 |
| 2d | 7 | 6.8 | — | 0.85 | 25 |
| 3c | 7 | 8.0 | 3.1 | 0.5 | 19 |
| 3d | 7 | 6.4 | 2.0 | 0.5 | 27 |
| 2a | 14 | 11.0 | 3.1 | 0.8 | 44 |
| 2b | 14 | 8.5 | 2.8 | 0.35 | 42 |
| 3a | 21 | 3.8 | 1.0 | 0.6 | 25 |
| 4a | 28 | 3.6 | 1.5 | 5.0 | 61 |
| 4b | 28 | 4.4 | 1.0 | 5.0 | 55 |
| 4c | 28 | 4.4 | 1.6 | 5.0 | 73 |

(a) Average zinc accumulation in solution after 7, 14, 21 and 28 days = 31, 43, 25 (one result only) and 63 µg.
(b) Metal in membranes of accumulators 4a, 4b and 4c were determined. See Table 16.
(c) See footnote (c) Table 16.

TABLE 15

Analysis of river water during Field Trials IV and V

| Day | Sample Procedure | pH | Cu | Pb | Cd | Zn |
|---|---|---|---|---|---|---|
| 2 | S | 8.3 | 0.01 | | 0.002 | 0.02 |
| 2 | P | 8.3 | 0.005 | | 0.0015 | 0.04 |
| 3 | D | — | 0.01 | | 0.0025 | 0.03 |
| 3 | P | — | 0.01 | | 0.0025 | 0.02 |
| 6 | P | 7.8 | 0.015 | | 0.001 | 0.02 |
| 6 | D | 7.9 | 0.015 | | 0.002 | 0.02 |
| 7 | D | 7.8 | 0.01 | | — | 0.02 |
| 8 | P | 8.3 | 0.01 | | 0.002 | 0.02 |
| 9 | P | 8.0 | 0.02 | | 0.002 | 0.04 |
| 10 | P | 8.4 | 0.01 | | 0.006 | 0.02 |
| 11 | S | 7.8 | 0.02 | | 0.001 | 0.02 |
| 11 | P | 7.9 | 0.02 | | 0.0025 | 0.02 |
| 12 | S | 7.9 | 0.02 | | — | 0.03 |
| 12 | P | 7.7 | 0.01 | | 0.0015 | 0.02 |
| 13 | P | 8.0 | 0.005 | | 0.002 | 0.02 |
| 13 | S | 8.3 | 0.005 | | 0.002 | 0.02 |
| 14 | S | 7.4 | 0.005 | | 0.001 | 0.08 |
| 15 | P | 7.7 | 0.02 | | 0.0005 | 0.02 |
| 15 | S | 7.8 | 0.01 | | 0.001 | 0.02 |
| 16 | S | 8.0 | 0.005 | not detected | 0.001 | 0.10 |
| 17 | P | 7.7 | 0.005 | | 0.0005 | 0.04 |
| 18 | P | 7.7 | 0.005 | | 0.0005 | 0.03 |
| 19 | P | 7.8 | 0.01 | | 0.0005 | 0.10 |
| 20 | P | — | 0.015 | | 0.0015 | 0.03 |
| 20 | D | 7.7 | 0.015 | | 0.001 | 0.05 |
| 21 | P | — | 0.015 | | 0.001 | 0.03 |
| 22 | D | — | 0.005 | | 0.0005 | 0.04 |
| 24 | P | — | 0.01 | | 0.0015 | 0.01 |
| 27 | D | — | 0.005 | | 0.0005 | 0.01 |
| 28 | D | — | 0.005 | | 0.0005 | 0.02 |
| 29 | D | — | 0.01 | | 0.0005 | 0.02 | aCode for S, P and D as in Table 13.

TABLE 16

Field Trials IV and V. Total metal accumulated (µg) in carbon tetrachloride-dithizone and in membranes over the 8 day period 11-12-74 to 19-12-74, and over the 4 week period 20-11-74 to 19-12-74.

| Accumulator | Metal in $CCl_4$ | Metal in | Total metal, |

TABLE 16-continued

| No. | -dithizone,A | membrane,B | A + B |
|---|---|---|---|
| COPPER | | | |
| R1 | 4.8 | 4.0 | 8.8 |
| R2 | 10.0 | 5.0 | 15.0 |
| R3 | 5.9 | 2.0 | 7.9 |
| R4 | 4.6 | 3.5 | 8.1 |
| R5 | 4.6 | 4.5 | 9.1 |
| R6 | 3.6 | 3.5 | 7.1 |
| R7 | 3.6 | 2.0 | 5.6 |
| 4a | 3.6 | 4.0 | 7.6 |
| 4b | 4.4 | 3.0 | 7.4 |
| 4c | 4.4 | 3.5 | 7.9 |
| LEAD | | | |
| R1 | 1.4 | 0.3 | 1.7 |
| R2 | 3.6 | 0.5 | 4.1 |
| R3 | 1.4 | 0.5 | 1.9 |
| R4 | 0.8 | 0.3 | 1.1 |
| R5 | 1.6 | 0.5 | 2.1 |
| R6 | 0.8 | 0.3 | 1.1 |
| R7 | 0.8 | 0.3 | 1.1 |
| 4a | 1.5 | 0.3 | 1.8 |
| 4b | 1.0 | 0.3 | 1.3 |
| 4c | 1.6 | 0.3 | 1.9 |
| CADMIUM | | | |
| R1 | 1.3 | 0.70 | 2.0 |
| R2 | 2.5 | 0.35 | 2.85 |
| R3 | 1.6 | 0.25 | 1.85 |
| R4 | 0.5 | 0.25 | 0.75 |
| R5 | 0.4 | 0.25 | 0.65 |
| R6 | 0.7 | 0.25 | 0.95 |
| R7 | 0.7 | 0.30 | 1.00 |
| 4a | 5.0* | 0.20 | |
| 4b | 5.0* | 0.30 | |
| 4c | 5.0* | 0.60 | |
| *suspect | | | |
| ZINC | | | |
| R1 | 15 | 80 | 95 |
| R2 | — | 85 | 85 |
| R3 | 25 | 70 | 95 |
| R4 | 15 | 75 | 90 |
| R5 | 15 | 85 | 100 |
| R6 | 15 | 85 | 100 |
| R7 | 20 | 50 | 70** |
| 4a | 60 | 215 | 275*** |
| 4b | 55 | 190 | 245 |
| 4c | 75 | 210 | 285 |

** = Average accumulation zinc after 8 days = 89 µg.
*** = Average accumulation zinc after 28 days = 268 µg.
(a) Accumulators R1 - R7 in river for 8 days - Field Trial V.
(b) Accumulators 4a, 4b & 4c in river for 4 weeks - Field Trial
(c) To date insufficient data are available on metal content of 'control'. A first order estimate of the amount of metal accumulated can be obtained by subtracting the following 'blank' or 'control' values from values quoted in Tables 12, 14 and 16. In some instances these 'first order' control values were greater than the amount of metal found indicating the problems of correlating results of initial field trials where low levels of metal were accumulated.
(i) accumulator control (i.e. accumulator prepared in the normal way, filled with trapping agent and stored in laboratory for 1 week); 2.5 µg copper, 1.2 µg lead, 0.55 µg cadmium, 10 µg zinc.
(ii) membrane blank (i.e. metal content of unused membrane of approximately equivalent weight to that used in accumularor): 0.3 µg copper, 0.4 µg lead, 0.05 µg cadmium, 4 µg zinc.

It was seen that accummulation of zinc had occurred over the four weeks period.

It is emphasised that accummulation trends are only likely to be observed when the amounts of accummulated metal are significantly greater than 'blank' and 'control' levels. (Note: This result refers to metal present in the carbon tetrachloride-dithizone mixture; subsequent work in Field Trial V showed that significant amounts of zinc were trapped in the membrane as well).

Insufficient data on the R. Esk were available to comment sensibly on whether or not it was likely that significant amounts of available copper would be accummulated. At a river pH of 7.5 to 8.5 (Table 15 above) and an alkalinity of ~100 mg/l as $CaCO_3$, equivalent to $2 \times 10^{-3}$ M bicarbonate (see Table 17 below), most of the copper will be complexed $CuCO_3$, in the absence of other complexing agents. Calculations (see below) show that, thermodynamically, $CuCO_3$ should react quantitivatively with dithizone. However, it is possible that other complexing agents such as amino acids, polypeptides and humic acids would compete for available copper and that complexes formed with these ligands are much less labile than $CuCO_3$. Obviously, further investigations of the chemical states of copper in the R. Esk were needed.

TABLE 17

Analysis of R. Esk (conducted by Lothians River Purification Board; ref. L.R.P. 61). Results expressed in mg/l.

| Sample No. | Date | Time | Total Hardness | Alkalinity | Sulphate | Chloride | B.O.D. | C.O.D. | Ca. | Mg. | Na. | K | Fe | Mn |
|---|---|---|---|---|---|---|---|---|---|---|---|---|---|---|
| 473 | 3.2.75 | 14.15 | 168 | 80 | 56.1 | 27 | 0.040 | 1.4 | 38.0 | 25.0 | 12.9 | 6.7 | 2.6 | 0.90 | 0.10 |
| 471 | 4.2.75 | 12.00 | 180 | 95 | 70.7 | 30 | 0.075 | 1.5 | 25.0 | 26.5 | 13.7 | 7.4 | 2.6 | 0.94 | 0.05 |
| 472 | 6.2.75 | 12.20 | 184 | 100 | 83.0 | 31 | 0.055 | 1.5 | 16.4 | 30.5 | 16.1 | 8.9 | 3.2 | 1.04 | 0.22 |
| 503 | 10.2.75 | 10.00 | 188 | 105 | 82.0 | 30 | 0.050 | 1.7 | 5.4 | 31.5 | 16.7 | 9.7 | 3.4 | 1.08 | 0.22 |
| 474 | 14.2.75 | 14.45 | 200 | 95 | 81.2 | 34 | 0.045 | 2.3 | 21.8 | 32.5 | 17.8 | 12.3 | 3.1 | 1.12 | 0.22 |

Field Trial V (and part of Field Trial IV)

A second 1 week reproducibility trial was run during the fourth week of Field Trial IV. In addition to analysing the carbon tetrachloride-dithizone solutions, the membranes were also analysed. The membranes from three 'four-week' accumulators from Field Trial IV were also analysed. The results are shown in Table 16 above, and, for the 1 week trial, are summarised as follows:

(i) The amounts of metal found in the carbon tetrachloride-dithizone were of the same order as those found in Field Trial III.

(ii) Significant quantities of metal were found in the membranes. With the exception of lead, these amounts were considerably greater than that found in membrane blanks. The amounts of copper and cadmium found in the membranes were about the same as, or slightly less than, those in the carbon tetrachloride-dithizone. However, considerably more zinc was found in the membrane than in the carbon tetrachloride-dithizone; this recently may reflect the greater amount of zinc present in the river (iii) There was more metal in the membranes of accumulators which had been in the river for four weeks than in the membranes of those which had been in the river for only one week.

While it is thought that most of the metal found in the membrane is present as 'precipitated' metal dithizonate it is possible that some metal could be present as small colloidal particles which adhere to the membrane surface, and are not removed when the membrane is washed briefly with water.

(iv) The results (Table 16) show that significant accumulation of zinc (in solution and membrane) occurred over a 4 week period; and that the accumulation was roughly as forecase for theory.

Other Analysis of R. Esk

Chemical analysis of R. Esk water was undertaken by the Lothians River Purification Board. Although the analysis was done after the trials were completed, the results (Table 17 above), are thought realistically to represent conditions during the trials.

Re-use of Membranes

One experiment was done to see whether there was any indication that the membranes ceased to function after a period of time in the river.

A used membrane taken from an accumulator which had been in the river for one week was washed and dried. It was then re-swollen in water and used in a standard laboratory experiment (accumulation from a 5 mg/l copper sulphate solution pH 4.5). The rate of accumulation was about two-thirds that for an accumulator with a new membrane. On the assumption that the dying and re-swelling procedure per se do not markedly affect permeability, this one result indicates that the membrane was still functional after one week's immersion in the river.

CALCULATIONS

Reaction of $CuCO_3$ with Dithizone

Consider the system copper in $5 \times 10^{-3}$ M bicarbonate, pH 7; 100 mg/l dithizone in carbon tetrachloride. Let copper dithizone be represented by $Cu(HD)_2$ and dithizone be represented by $H_2D$. The possible active species are:
$H_2D$, $HD^{31}$, $D^{2-}$; $Cu^{2+}$, $CuCO_3$:$HCO_3^-$, $CO_3^{2-}$.
The values for $k_1$, $k_2$, etc. were obtained from Sillen and Martin, Stability Constants of Metal-Ion complexes, Chem, Soc. Special Publication No. 17 (1964).

Dissociation of dithizone:

$$H^+ + D^{2-} \longrightarrow HD^-;$$

$$k_1 = \frac{[HD^-]}{[H^+][D^{2-}]} = 10^{15}$$ (xix)

$$H^+ + HD^- \longrightarrow H_2D;$$ (xx)

$$k_2 = \frac{H_2D}{[H^+][HD^-]} = 10^{4.55}$$

At pH = 7, $[H^+] = 10^{-7}$

Therefore $\frac{[HD^-]}{[D^{2-}]} = 10^{15} \times 10^{-7} = 10^8$ (xxi)

and $\frac{[H_2D]}{[HD^-]} = 10^{4.55} \times 10^{-7} = 10^{-2.45}$ (xxii)

Consider $Cu^{2+}$ in water at pH7 and $[HCO_3^-] = 5 \times 10^{-3}$ M $$Cu^{2+} + CO_3^{2-} \longrightarrow CuCO_3;$$ (xxiii)

$$k_4 = \frac{[CuCO_3]}{[Cu^{2+}][CO_3^{2-}]} = 10^{6.8}$$

$$H^+ + CO_3^{2-} \longrightarrow HCO_3^-;$$ (xxiv)

$$k_5 = \frac{[HCO_3^-]}{[H^+][CO_3^{2-}]} = 10^{10.3}$$

At pH7 $[H^+] = 10^{-7}$ $$\frac{[HCO_3^-]}{[CO_3^{2-}]} = 10^{-7} \times 10^{10.3} = 10^{3.3}$$ (xxv)

-continued $$[CO_3^{2-}] = \frac{[HCO_3^-]}{10^{3.3}} = \frac{5 \times 10^{-3}}{2 \times 10^3} = 2.5 \times 10^{-6} M$$

Now $\frac{[CuCO_3]}{[Cu^{2+}][CO_3^{2-}]} = 10^{6.8}$ $$\frac{[CuCO_3]}{[Cu^{2+}]} = 15.8$$ (xxvi)

Therefore, at pH 7 the predominant species resulting from dithizone and available for reaction with metal ions was $HD^-$.

Reaction of $Cu^{2+}$ with dithizone.

The concentration of dithizone in carbon tetrachloride used in the field trials was 100 mg/l (= $0.39 \times 10^{-3}$ molar). This value is used in the following calculation.

$$Cu^{2+} + 2HD \longrightarrow Cu(HD)_2;$$ (xxvii)

$$k_3 = \frac{[Cu(HD)_2]}{[Cu^{2+}][HD^{-2}]} = 10^{22.3}$$

$$\frac{[Cu(HD)_2]}{[Cu^{2+}]} = 10^{22.3} \times 0.152 \times 10^{-6}$$ (xxviii)

$$= 0.3 \times 10^{-16}$$

At equilibrium the ratio of copper dithizonate to copper carbonate complex is given by:

$$\frac{[Cu(HD)_2]}{[CuCO_3]} = \frac{[Cu(HD)_2]}{[Cu^{2+}]} \times \frac{[Cu^{2+}]}{[CuCO_3]} = \frac{0.3 \times 10^{16}}{15.8}$$

$$= 1.9 \times 10^{14}$$

This high ratio indicates that $CuCO_3$ should (thermodynamically) react quantitatively with dithizone at equilibrium; earlier laboratory work measured the kinetics of this reaction.

The value of $1.9 \times 10^{14}$ is calculated for conditions at pH7. It is assumed that the rate of reaction of $Cu^{2+}$ with dithizone is not pH-dependent (an assumption which is not strictly true), then at pH 8.5, when the ratio of $CuCO_3$ to $Cu^{2+}$ is about 99:1 in $50 \times 10^{-3}$ M bicarbonate, the ratio of $Cu(HD)_2$ to $CuCO_3$ will be about $10^{12}$ which is still sufficiently high not to affect the argument.

(III) CONCLUSION

Our river experiments have shown that significant amounts of metals are accumulated from very dilute streams in relatively short times, and that the accumulated metal is easily analysed by conventional methods such as atomic absorption spectrometry. For example, an accumulator fitted with a 44 cm² area cellulose membrane and filled with 400 ml of a carbon tetrachloride solution containing 100 mg/l dithizone accumulated about 89 µg zinc after 7 days' immersion in a river whose average concentrations of zinc during this time was 0.03 µg/ml. After 82 days' immersion, the amount accumulated was about 268 µg.

Our tests also indicate that considerable improvements can be obtained e.g. by stirring the aqueous layer in contact with the membrane. This can be done by a simple stirrer like device.

In many practical situations it is likely that sudden increases in metal ion concentration (surges) in a river will occur. The amount of metal accumulated from surges can be estimated by the application of equation (iv) above. For example, consider an accumulator with P.A. = $10^3 cm^3 day^{-1}$ immersed in a stream whose background level of $Hg^{2+}$ is $3 \times 10^{-5} \mu g/ml$. If the stream is subjected to a surge of $10^{-1} \mu g/ml Hg^{2+}$ for 2.4 h in a 30 day period, 90.7% of the total amount of metal accumulated would have resulted from the surge. If the surge lasted for one day, or 10 periods of 2.4 h, then 99.2% of the total amount of metal accumulated would have originated from the surge.

The method and apparatus of the invention are not restricted to the use of dithizone and carbon tetrachloride. The material from which the body of the accumulator device is made should not contain metals which can be removed, albeit slowly by the 'trapping agent'. A wide range of other complexing agents and of solvents with low water solubilities can be used, depending on the metal(s) being investigated. Similarly, other polymeric membranes than those specifically referred to can be used subject to their compatibility with the organic liquid medium or solvent and the 'trapping' agent, their ability to allow the required diffusion processes to occur and their resistance to biodegradation.

The accumulator device can be located for example, on a river bed. However the device need not be immersed directly in the river or estuary under test. It is convenient to locate the device in a bath or other container placed, for example, on the river bank, and to pump the water through the bath or container in a regular fashion.

It should also be noted that the method and apparatus for metal ion detection can be applied to metal prospecting in precisely the same way as they have been used to determine metal pollution.

Figure 22:
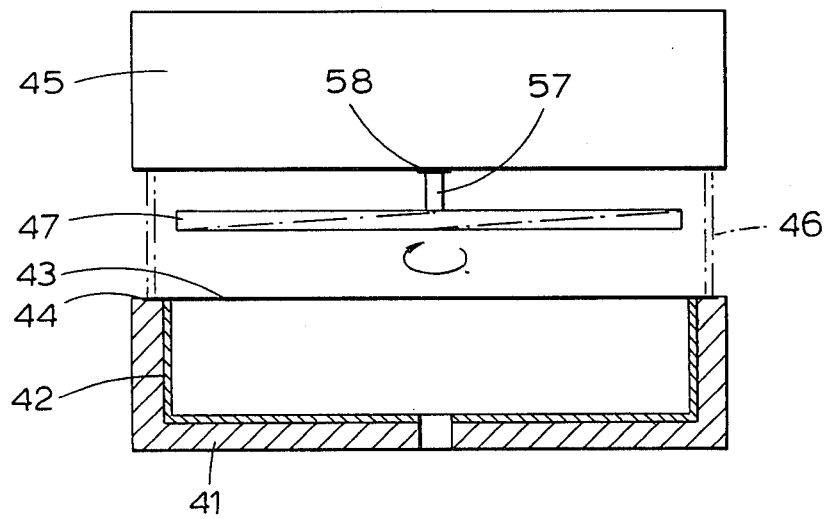
Figure 23:
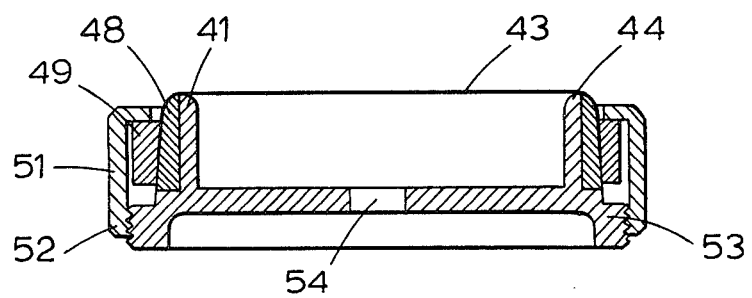
Figure 24:
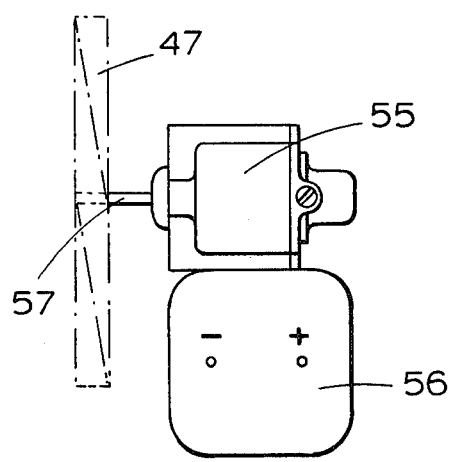

One improvement in the design of the accumulator is to incorporate a stirring device close to the membrane surface. Mechanical stirring in, for example, slow-moving streams minimises the boundary layers referred to earlier (FIG. 4), and increases the rate of diffusion of metal ions across the membranes. Such a device results in a more constant rate of accumulation than may be found in the devices described above. A suitable design is shown in FIGS. 22 and 23 of the accompanying drawings. A metal housing 41 is provided with an interior lining 42 of glass or other inert material which is uncontaminated by metal. A membrane 43 is secured to the mouth 44 of the housing 41 as shown below in FIG. 23. A motor block 45 is supported above the housing 41 by several connecting rods 46. A motor 55 drives a stirrer blade 47 and is energised by a long-life battery 56 (FIG. 24). FIG. 23 is a more detailed sectional elevation of the housing 41 which is of stainless steel (the glass or like lining 42 is omitted for clarity). The membrane 43 is held between plastics annuli 48 and 49 respectively.

A cap 51 is threadedly engaged as its lower end 52 with corresponding threading 53 on the outside wall of the housing 41. A filling aperture 54 with a closure means not shown is provided in the base of the housing.

FIG. 24 is a side view showing the motor 55 and long-life battery 56 forming part of the motor block 45 (cover omitted). The stirrer 47 has a shaft 57 which enters the motor block 45 through a leak-proof seal 58.

I claim:

1. A method of monitoring the metal content in a water system comprising the steps of allowing continuous samples of said water system to contact one side of a porous membrane capable of allowing said metal ions to diffuse therethrough, maintaining in contact with the other side of said porous membrane an organic liquid medium containing a trapping agent therein, capable of forming with said metal ions complexes which are soluble in said organic liquid medium; and removing at intervals samples of said organic liquid medium containing said complexes and analysing said samples to determine the accumulation of said metal ion over a predetermined period.

2. A method according to claim 1, wherein said trapping agent is dithizone.

3. A method according to claim 1, wherein said trapping agent is selected from the group consisting of cupferron, acetylacetone, dibenzoylmethane, thenoyltrifluoroacetone, 8-hydroxyquinoline, benzildioxime and 1-(2-pyridylazo)-2-naphthol.

4. A method according to claim 1, wherein said trapping agent is dithizone and said organic liquid medium is carbon tetrachloride.

5. A method according to claim 1, wherein said trapping agent is selected from the group consisting of cupferron, acetylacetone, dibenzoylmethane, thenoyltrifluoroacetone, 8-hydroxyquinoline and 1-(2-pyridylazo)-2-naphthol, and said organic liquid medium is selected from the group consisting of chloroform, benzene, diethylether, carbon tetrachloride and isoamyl alcohol.

6. A method according to claim 1, wherein said porous membrane is composed of a material selected from the group consisting of regenerated cellulose, vinyl chloride homopolymers and copolymers, polyvinylidene fluoride, acrylonitrile-polyvinylchloride and polytetrafluoroethylene.

7. An apparatus for monitoring the metal content of a water system, comprising an impermeable housing provided with an opening, a porus membrane disposed over the opening, said membrane constituting a permeable aqueous medium-organic medium interface, means to secure said membrane to said housing at said opening whereby to constitute a permeable ion barrier at said opening and further comprising a concrete block provided with an opening for receiving said device and allowing water to flow freely through said device and said concrete block, means anchoring said device within said concrete block at the mouth of said opening and means supporting said concrete block with said device at a chosen location in a water system, an organic liquid medium disposed within said housing filling said housing to a level at which said organic liquid medium contacts said membrane, and a trapping agent within said organic liquid medium to form a complex soluble in said organic liquid medium with at least one class of metal ion diffusing through said membrane from an aqueous medium in contact with the outside of said membrane.

* * * * *